United States Patent
Yamamoto et al.

(10) Patent No.: US 10,557,815 B2
(45) Date of Patent: Feb. 11, 2020

(54) PARTICULATE MATTER DETECTION SENSOR

(71) Applicant: DENSO CORPORATION, Kariya, Aichi-pref. (JP)

(72) Inventors: Masahiro Yamamoto, Kariya (JP); Masayuki Tamura, Kariya (JP); Go Miyagawa, Kariya (JP); Toru Katafuchi, Kariya (JP); Takehito Kimata, Kariya (JP); Yuto Tamei, Kariya (JP)

(73) Assignee: DENSO CORPORATION, Kariya (JP)

( * ) Notice: Subject to any disclaimer, the term of this patent is extended or adjusted under 35 U.S.C. 154(b) by 111 days.

(21) Appl. No.: 15/759,947

(22) PCT Filed: Sep. 14, 2016

(86) PCT No.: PCT/JP2016/077034
§ 371 (c)(1),
(2) Date: Mar. 14, 2018

(87) PCT Pub. No.: WO2017/047606
PCT Pub. Date: Mar. 23, 2017

(65) Prior Publication Data
US 2018/0266936 A1 Sep. 20, 2018

(30) Foreign Application Priority Data

Sep. 15, 2015 (JP) .................................. 2015-182218

(51) Int. Cl.
*G01N 27/407* (2006.01)
*G01N 27/04* (2006.01)
(Continued)

(52) U.S. Cl.
CPC ..... *G01N 27/4071* (2013.01); *G01N 15/0606* (2013.01); *G01N 15/0656* (2013.01);
(Continued)

(58) Field of Classification Search
CPC ............. G01N 1/2252; G01N 15/1031; G01N 15/1056; G01N 27/04; G01N 27/045;
(Continued)

(56) References Cited

U.S. PATENT DOCUMENTS

| 2011/0259079 | A1 | 10/2011 | Maeda et al. |
| 2012/0047993 | A1* | 3/2012 | Tokuda .............. G01N 15/0656 73/23.33 |
| 2012/0085146 | A1 | 4/2012 | Maeda et al. |

FOREIGN PATENT DOCUMENTS

| JP | 60-196659 | 10/1985 |
| JP | 2006-026696 | 2/2006 |

(Continued)

*Primary Examiner* — Benjamin R Schmitt
(74) *Attorney, Agent, or Firm* — Nixon & Vanderhye P.C.

(57) ABSTRACT

A sensor element which has a pair of positive and negative detection electrodes disposed on a surface of an insulation body as a detecting portion and a cover body configured to cover an opening of a cylindrical housing. The cover body is provided with gas inlet and outlet holes via which the measuring gas is introduced and discharged. The pair of detection electrodes have a plurality of wire electrodes. The wire electrodes electrically connected to the positive electrode and the wire electrodes electrically connected to the negative electrode are alternately arranged in parallel. Any one of a first insulation layer which is a narrow electrode interval Dn and a second insulation layer which is a wide electrode interval Dw, arranged between adjacent wire electrodes, and the first insulation layer arranged in a center part of the detecting portion.

20 Claims, 18 Drawing Sheets

(51) Int. Cl.
*G01N 15/10* (2006.01)
*G01N 27/12* (2006.01)
*G01N 15/06* (2006.01)
G01M 15/10 (2006.01)
G01N 15/00 (2006.01)

(52) U.S. Cl.
CPC ..... *G01N 15/1031* (2013.01); *G01N 15/1056* (2013.01); *G01N 27/045* (2013.01); *G01N 27/122* (2013.01); *G01M 15/102* (2013.01); G01N 2015/0046 (2013.01)

(58) Field of Classification Search
CPC .... G01N 27/12; G01N 27/122; G01N 27/125; G01N 27/128; G01N 27/407; G01N 27/4071; G01N 33/0027; G01M 15/10; G01M 15/102
USPC ................................. 73/28.01, 31.03, 31.05
See application file for complete search history.

(56) References Cited

FOREIGN PATENT DOCUMENTS

| | | |
|---|---|---|
| JP | 2012-078130 | 4/2012 |
| JP | 2012-168143 | 9/2012 |
| JP | 2012-220257 | 11/2012 |

\* cited by examiner

PARTICULATE MATTER DETECTION SENSOR

CROSS REFERENCE TO RELATED APPLICATIONS

This application is the U.S. national phase of International Application No. PCT/JP2016/077034 filed on Sep. 14, 2016 which designated the U.S. and claims the benefit of priority of earlier Japanese Patent Application No. 2015-182218 filed on Sep. 15, 2015, and Japanese Patent Application No. 2016-142329 filed on Jul. 20, 2016, the entire contents of each of which are hereby incorporated by reference.

TECHNICAL FIELD

The present disclosure relates to a particulate matter detection sensor which detects particulate matter contained in a measuring gas, and more particularly relates to a sensor which detects particulate matter in an exhaust gas emitted from an internal combustion engine.

RELATED ART

Conventionally, an electrical resistance type particulate matter detection sensor is used as a particulate matter detection sensor, in order to detect an amount of particulate matter (specifically PM) in an exhaust gas emitted from an internal combustion engine.

For example, a particulate matter detection sensor disclosed in JP literature 1 is provided with a laminate structured insulating body, at least one part of the insulating body having a detection electrode embedded in the insulating body, and a sensor element which has a surface in which detection electrodes are exposed thereon as a detecting portion.

The sensor element is maintained inside a cover body which is provided with exhaust gas an inlet-holes. Detection electrodes of different polarities are alternately disposed with an insulation layer intervened therebetween on the detecting portion of the sensor element, into which the exhaust gas flows. Once an electrostatic field is formed by application of a voltage, charged particulate matter is attracted and this particulate matter accumulates between electrodes. An amount of particulate matter contained in the exhaust gas may be thus detected from a change in a resistance value between the electrodes. A comb-shaped electrode formed by printing on a surface of the insulating body may also be used as the detecting portion.

The particulate matter detection sensor described above is mounted on an exhaust pipe of a diesel engine, for example, and is used for malfunction diagnosis of an exhaust gas purifying apparatus equipped with a diesel particulate matter filter (referred to as DPF hereon).

CITATION LIST

Patent Literature

[Patent Literature] JP2012-78130A

A particulate matter detection sensor has an insensitive period which exists at a start-up point of a sensor until the sensor output has reached a predetermined value by accumulation of particulate matter between electrodes of a detecting portion. As a result, the shorter the start-up time is the earlier the detection of particulate matter may be performed. That is, intervals between the detection electrodes may be narrow in order to increase a sensitivity of the sensor, for the particulate matter detection sensors used for malfunction diagnosis. However, when only electrode intervals are configured to be narrow without changing the size or the number of the detection electrodes, an essential detection area becomes smaller, and if a position in which exhaust gas flows is misaligned when the exhaust gas is introduced inside the cover body, the sensitivity of the sensor will in contrast decrease. In this regard, effects of dimensional precision of the cover body and assembly precision of the sensor are increased, thus, a difference in the sensitivity occurring between sensors also increases.

In order to avoid such issues mentioned above, if a number of detection electrodes provided is increased and a detection area is configured to be larger, a production cost will also increase due to a higher number of laminate layers and an increased usage of electrode materials.

On the other hand, particulate matter adhered to a wall inside an exhaust pipe may detach therefrom, for example, and coarse particles having a larger particle diameter than the usual size may be formed and emitted. In this case, if the electrode interval between detection electrodes is narrow, an acute increase of the sensor output will occur frequently. As a consequence, a precision of diagnosing malfunctions of a DPF (Diesel particulate filter) decreases, and there is a concern of DPF malfunction and erroneous diagnosis occurring.

In view of the above issues, the present disclosure aims to provide a particulate matter detection sensor which has a good sensor sensitivity, a difference in sensitivity between sensors is small, and a probability of the occurrence of a sensor output changing due to adherence of particulate matter is low, with superior productivity and reliability.

SUMMARY

Solution to Problem

A mode of the present disclosure is a particulate matter detection sensor provided with a sensor element for detecting particulate matter contained a measuring gas. The sensor element is provided with one pair of detection electrodes which consist of a positive electrode and negative electrode, the detection electrodes being disposed on a surface of an insulating body the insulation body being a detecting portion, and a cover body configured to cover an opening of a cylindrical housing which accommodates the sensor element. The cover body is provided with a gas inlet/outlet holes. The measuring gas being introduced and discharged through the gas inlet/outlet holes.

Each of the detection electrodes composing the one pair of the detection electrodes is provided with a plurality of wire electrodes exposed on a front surface of the detecting portion. The wire electrode being electrically connected to the positive electrode and the wire electrode being electrically connected to the negative electrode are alternately disposed in parallel to each other. Either one of a first insulation layer and a second insulation layer is disposed between two mutually adjacent electrodes, among the wire electrodes, the first insulation layer configuring an electrode interval $Dn$ as an interval between two mutually adjacent electrodes of the detection electrodes, and the second insulation layer configuring an electrode $Dw$. The electrode interval $Dw$ is a wider interval than the electrode interval $Dn$ which is a narrow interval. The second insulation layer provided with a plurality of insulation layers having different layer thicknesses. The first insulation layer is provided in a center part of the detecting portion 11.

It is to be understood that symbols in the summary and claims are used to show a corresponding relation between specific means as a mode described in preferred embodiments described herein after and do not limit a technical scope of the disclosure.

[Effects]

The particulate matter detection sensor is provided with the pair of the electrodes of the detecting portion of the sensor element into which the measuring gas is introduced, and any one of the first insulation layer and the second insulation layer intervened between a plurality of the wire electrodes which are mutually adjacent to each other. The interval between the two wire electrodes adjacent to each other is either one of the electrode interval Dn being the narrow interval and the electrode interval Dw which is wider electrode interval than the narrow electrode interval Dn.

Since the center part of the detecting portion has the narrow electrode interval Dn, once the measuring gas which flows from the gas inlet/outlet holes of the cover body is introduced thereto, particulate matter is instantly detected. Additionally, in providing the wide electrode interval Dw section, a detection area is enlarged even when a position in which the measuring gas is introduced (specifically, a gas flow position) is misaligned, and a decrease in the sensitivity of the sensor is thus suppressed. Also, if the sensor is configured with only the narrow intervals Dn, electricity is easily conducted between the pair of electrodes and an acute increase of the sensor output also occurs easily when coarse particles flow. However, since the electrode interval Dw which is wider than the electrode interval Dn is provided, the acute increase of the sensor output is suppressed.

According to the mode, a desirable sensor sensitivity is maintained, and while suppressing a difference in the sensitivity between sensors, an output variation due to coarse particles is also decreased, and a detection precision may be enhanced. Furthermore, a probability of the sensor output changing due to adhesion of the coarse particles is decreased without an increase of man-hours and an amount of materials used for electrodes, thus a particulate matter detection sensor having superior productivity and reliability may be actualized.

BRIEF DESCRIPTION OF DRAWINGS

In the accompanying drawings.

EMBODIMENTS

First Embodiment

Figure 1:
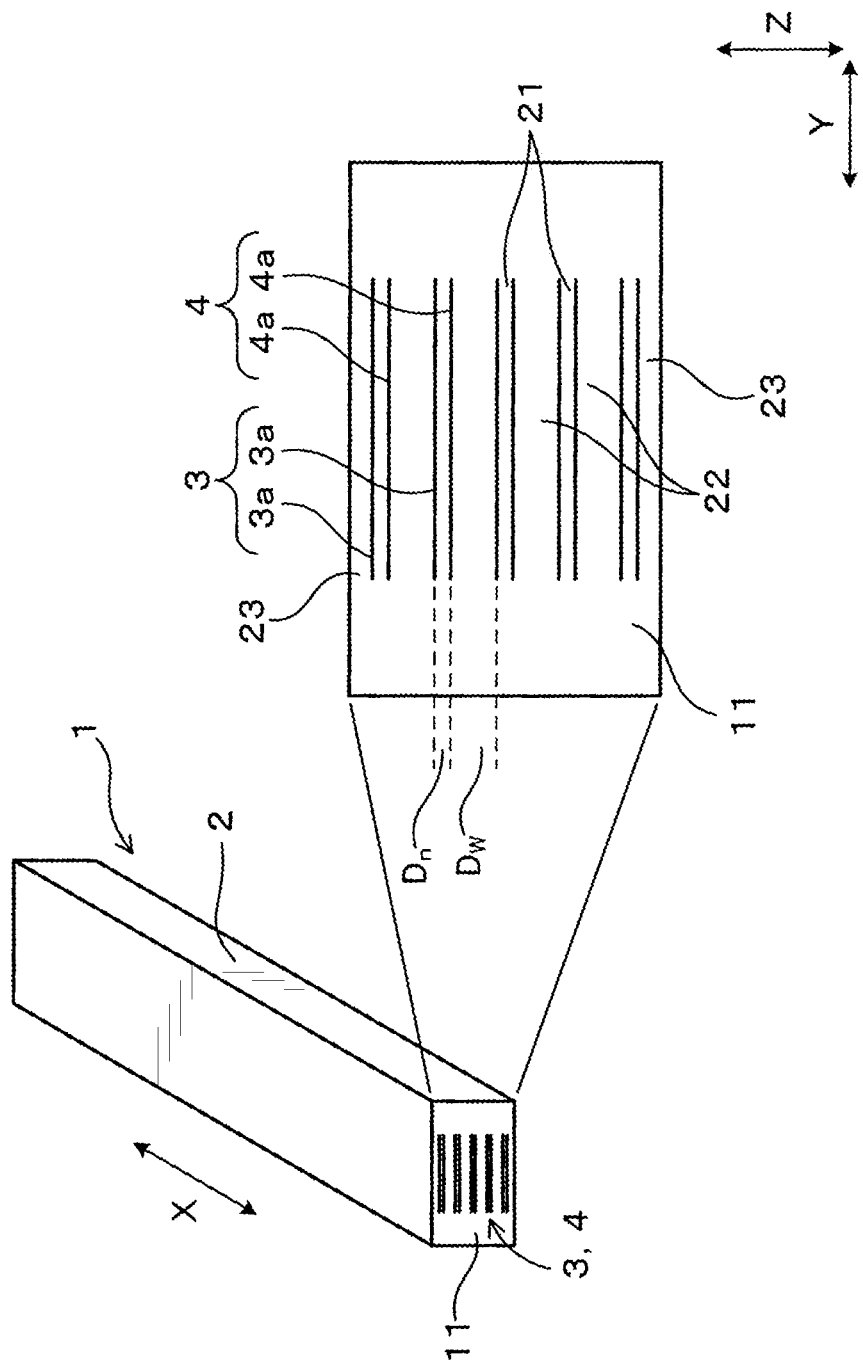
FIG. 1 is an overall perspective view and an enlarged view of a major part of a basic configuration of a sensor element of a particulate matter detection sensor according to a first embodiment.
Figure 2:
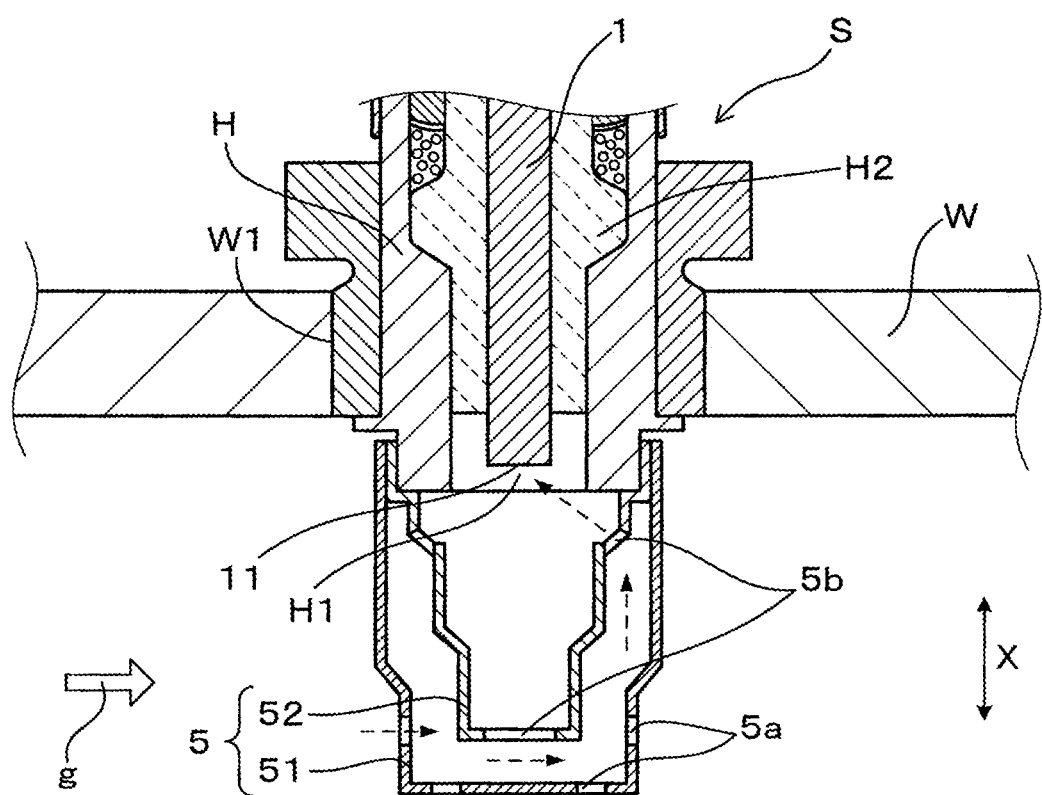
FIG. 2 is a cross section view in an axial direction showing a schematic configuration of the particulate matter detection sensor according to the first embodiment.

Next, an embodiment of a particulate matter detection sensor will be described with reference to the figures. In FIGS. 1 and 2, a basic configuration of the particulate matter detection sensor S according to a first embodiment is provided with a laminate-type sensor element 1 which has a detecting portion 11 configured on a front end thereof. The sensor 1 detects particulate matter contained in a measuring gas. The measuring gas is combustion exhaust gas emitted from an internal combustion engine, for example, a diesel engine, which contains minute particulate matter (referred to as PM hereon), for example, soot which has conductivity. The particulate matter detection sensor S is mounted on a wall W of an exhaust pipe of the internal combustion engine, and configures a malfunction diagnosis system of an exhaust gas purifying apparatus equipped with a DPF, for example.

As shown in FIG. 1, the sensor element 1 has a rectangular shaped insulating body 2 and a pair of detection electrodes 3 and 4 which consists of a positive electrode and a negative electrode as the detecting portion 11 disposed on the front end of the sensor element 1. For example, the detection electrode 3 is the positive electrode and the detection electrode 4 is the negative electrode. Each of the detection electrodes 3 and 4 are provided with a plurality of wire electrodes 3a and 4a which are exposed on a front surface of the detecting portion 11.

It is noted a length wise direction of the insulating body 2 is an element length direction X, a line length direction of the wire electrodes 3a and 4a of the detecting portion 11 is an element width direction Y, and a lamination direction which is orthogonal to the Y direction is an element thickness direction Z.

The plurality of wire electrodes 3a and 4a are arranged so that the wire electrode 3a electrically connected to the detection electrode 3 which is the positive electrode and the wire electrode 4a electrically connected to the detection electrode 4 which is the negative electrode are alternately arranged in parallel. The pair of wire electrodes 3a and 4a which are adjacent to each other are formed in plurality. Either one of a first insulation layer 21 or a second insulation layer 22 is disposed between the two adjacent wire electrodes 3a and 4a. A layer thickness of the first insulation layer 21 is formed to be thinner than a layer thickness of the second insulation layer 22. As a result, the two adjacent wire electrodes 3a and 4a with the first insulation layer 21 intervened therebetween have an electrode interval Dn. Additionally, the two adjacent wire electrodes 3a and 4a with the second insulation layer 22 intervened therebetween have an electrode interval Dw. The electrode interval Dw is a wider interval than the electrode interval Dn which is a narrow interval. It is noted that, the electrode Dn which is a narrow interval among the electrode intervals Dn and Dw may also be referred to as a first interval, and the interval Dw which is wider than the interval Dn may also be referred to as a second electrode interval. A third insulation layer 23 is arranged on an outer-side of the pair of electrodes 3 and 4 of the detecting portion 11, in the element thickness direction Z. A configuration of the detecting portion 11 is described in detail hereafter.

The particulate matter detection sensor S coaxially accommodates the sensor element 1 inside a cylindrical housing H, and the detecting portion 11 arranged inside a front opening H1 of the cylindrical housing H is protected by a cover 5 body which is mounted so that the front opening H1 of the cylindrical housing H is covered, as shown in FIG. 2. The particulate matter detection sensor S is fixed to a thread hole W1 provided on the exhaust pipe wall W of the internal combustion engine, for example, by a thread member H2 which is provided on an outer circumference of the cylindrical housing H.

The cover body 5 is a double container shape consisting of co-axially disposed outer cover 51 and inner cover 52. A plurality of gas inlet and outlet holes 5a and 5b are provided to surround an axis with an equal distance therebetween on a bottom portion and a side surface of each of the covers 51 and 52. The gas inlet and outlet holes 5a are provided on the outer cover 51 in a plurality of positions on a lower side surface and a bottom section of an outer circumference thereof. The gas inlet and outlet holes 5b are provided on the inner cover 52 in a plurality of positions on an upper side surface and in 1 position in a center part of a bottom section thereof.

A flow direction g in which the combustion exhaust gas flows into the exhaust pipe (a left to right direction in the figure) is a direction which is orthogonal to the element length direction X (a vertical direction in the figure). The length direction X is an axial direction of the particulate matter detection sensor S. The combustion exhaust gas flows from the gas inlet/outlet holes 5a of the lower side surface of the outer cover 51 to an inside of the cover body 5. Thereafter, the gas flows via a route formed between the outer cover 51 and the inner cover 52, and passes through the gas inlet/outlet hole 5b on the upper side surface of the inner cover 52 to be guided into the detecting portion 11 from a tip end entrance of the cylindrical housing H which opposes the detecting portion 11.

The particulate matter detection sensor S is mounted downstream of the DPF mounted in the exhaust pipe, for example, not shown in figures, and detects particulate matter which slips through the DPF. The particulate matter detection sensor S may configure a part of the DPF malfunction diagnosis system.

A shape of the cover body 5 and disposed position of the gas inlet/outlet holes 5a and 5b, shown in FIG. 2, are one example and may be suitably changed. The cover body 5 may be configured so that combustion exhaust gas flowing inside from gas inlet/outlet holes 5b of the inner cover 52 is guided towards a center part of the detecting portion 11. In general, the sensor 1 is preferably configured so that the gas inlet/outlet hole 5b of the inner cover 52 is positioned near to a lower section of the detecting portion 11 and the combustion exhaust gas flowing from the gas inlet/outlet hole 5b passes through the lower section of the center part of the detecting portion 11, as shown. Additionally, the respective gas inlet/outlet holes 5a and 5b are configured with a distance from each other in an axial direction or radial direction, to avoid gas directly flowing from the gas inlet/outlet hole 5a of the outer cover 51 to the gas inlet/outlet-hole 5b of the inner cover 52.

Figure 3:
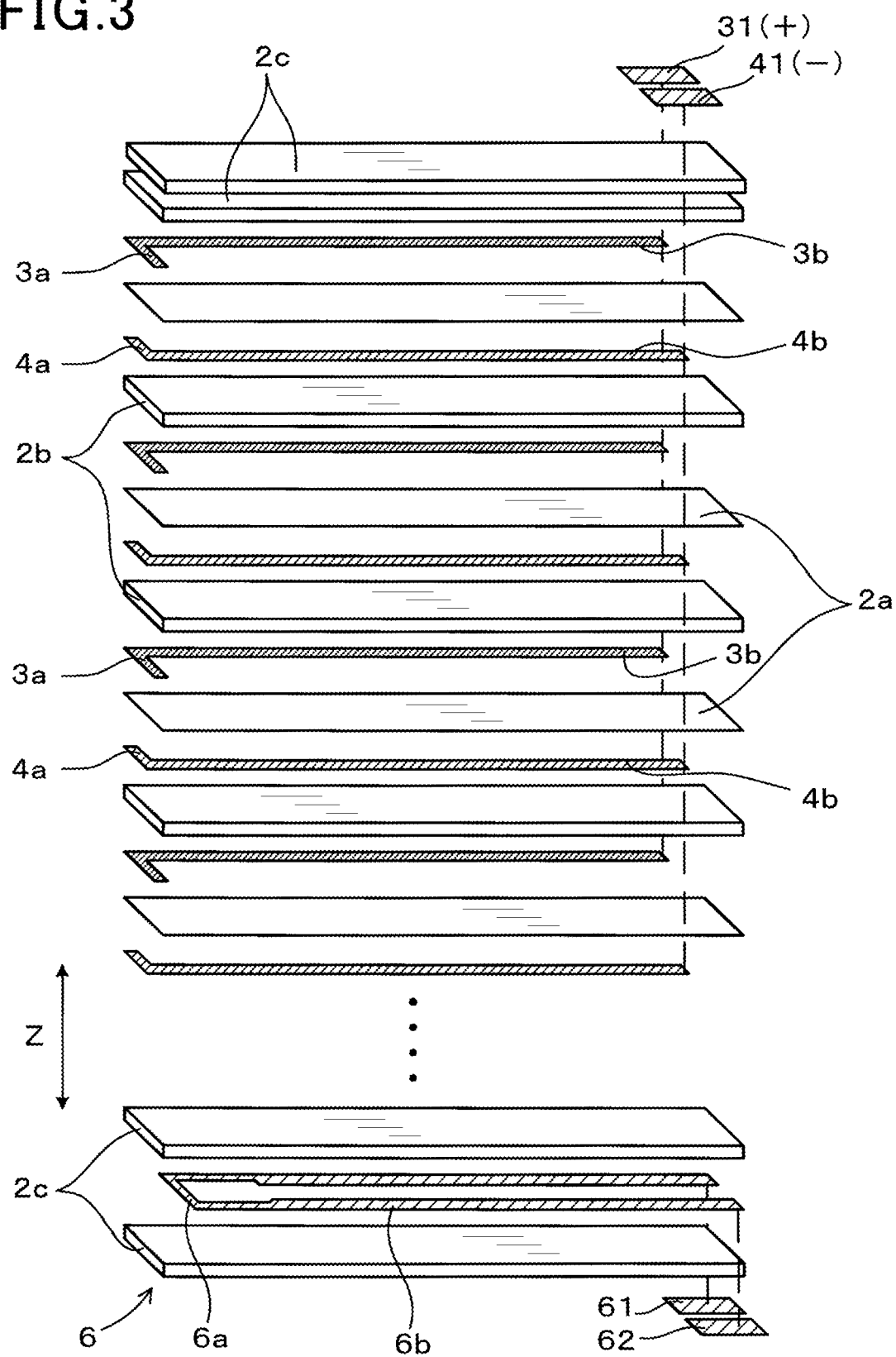
FIG. 3 is an exploded perspective view showing an example of the sensor element of the particulate matter detection sensor according to the first embodiment.

The sensor element 1 is configured of the insulating body 2 of laminated ceramic green sheets 2a to 2c which have electric insulating properties and the wire electrodes 3a and 4a alternately disposed between the green sheets 2a to 2c as shown in FIG. 3. The wire electrodes 3a and 4a are the detection electrodes 3 and 4. The green sheet 2a which is the first insulation layer 21 or the ceramic green sheet 2b which is the second insulation layer is arranged between the adjacent wire electrodes 3a and 4a. At this point, the ceramic green ceramic sheet 2a and the ceramic green sheet 2b, for example, are disposed to be alternately laminated in the element thickness direction Z, in order to provide a configuration shown in FIG. 1. The ceramic green sheet 2*a* corresponds to the narrow electrode interval Dn. A sheet thickness of the ceramic green sheet 2*a* is formed thinner than a sheet thickness of ceramic green sheet 2*b* which corresponds to the wide electrode interval Dw.

The plurality of ceramic green sheets 2*c* which form the third insulation layer 23 are disposed on a respective top layer and bottom layer of the laminate body. A heater electrode 6*a* and leading electrode 6*b* are arranged between the plurality of green sheets 2*c* on a lower-layer side to configure a heater 6. Terminal electrodes 31 and 41 are formed on a top surface of the top layer ceramic green sheet 2*c* at an end portion which opposes a side in which the wire electrodes 3*a* and 4*a* are disposed. Terminal electrodes 61 and 62 used for the heater 6 are formed on a lower surface of the bottom ceramic green sheet 2*c*. The heater electrode 6*a* is provided to correspond with the wire electrodes 3*a* and 4*a*, and configured to heat an entire detecting portion 11. The particulate matter detection sensor S supplies power to the heater 6 when the sensor element 1 is operating, eliminates water and particulate matter on the surface of the detecting portion 11 and prevents erroneous detection.

The wire electrodes 3*a* and 4*a* are formed on top of the ceramic green sheets 2*a* to 2*c* by screen printing and extended to another end side by leading electrodes 3*b* and 4*b*. The leading electrodes 3*b* and 4*b* are formed along a side end section of the ceramic green sheets 2*a* and 2*b*. It is noted that the wire electrodes 3*a* and 4*a* are preferably configured so that a portion which is exposed to a surface of the insulating body 2 is formed as a linear shaped electrode. For example, one side of the wire electrodes 3*a* and 4*a* may be configured as a rectangle or trapezoid shaped electrode film which is embedded between the ceramic green sheets 2*a* to 2*c*. The leading electrodes 3*b* and 4*b* are provided on different surfaces of side surface edge sections of the ceramic green sheets 2*a* to 2*c* and connected to the top terminal electrodes 31 and 41 through a conductor portion which is not shown in the figures. The conductor portion is formed on another end side thereof in the element thickness direction Z. A position in which the leading electrodes 3*b* and 4*b* are connected is shown with a broken line in the figures.

Insulation materials, for example, alumina, magnesia, titania and mullite, or known ceramic materials, for example, dielectric body materials for example, titanic acid or valium which have a high permittivity, mixed with alumina or zirconia for example, can be used as materials used to form the ceramic green sheets 2*a* to 2*c*. Metal materials, for example, aluminum, gold, platinum and tungsten, or metal oxide materials, for example, ruthenium oxide, or known conductive material, for example, perovskite structured conductive oxide materials are used for the wire electrodes 3*a* and 4*a*.

Figure 4:
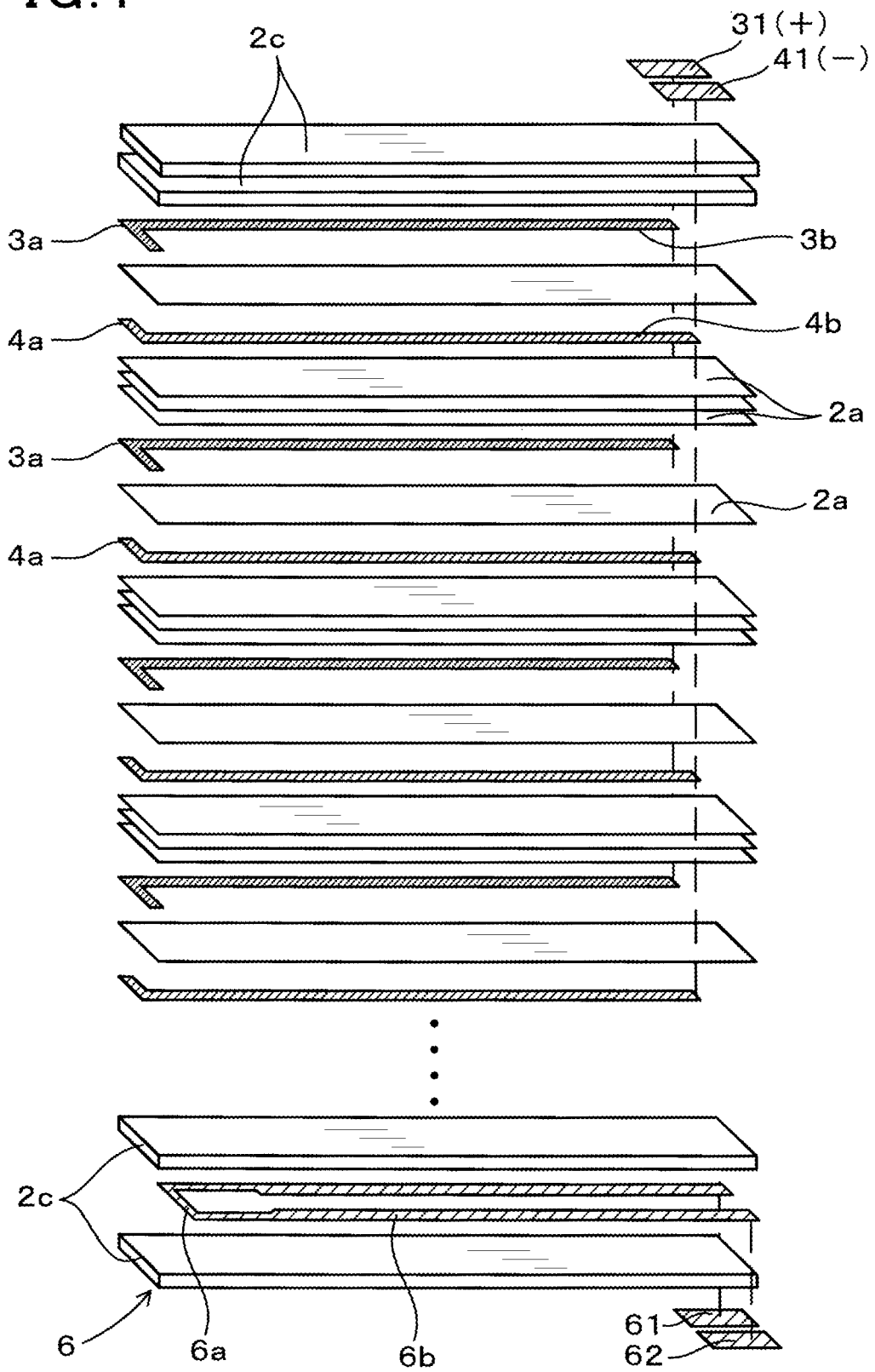
FIG. 4 is an exploded perspective view showing an example of the sensor element of the particulate matter detection sensor according to the first embodiment.

The ceramic green sheets 2*a* and 2*b* are a same rectangular shape, which may be formed by changing the sheet thickness of the same material. As shown in FIG. 4, the first insulation layer 21 and the second insulation layer 22 may be configured using one type of ceramic green sheet 2*a*. In this case, the second insulation layer 22 corresponding to the wide electrode interval Dw is formed by combining a plurality of thin ceramic green sheets 2*a* (for example 3) which have the same sheet thickness as ceramic green sheet 2*b*, shown in FIG. 3. Other configurations are as shown in FIG. 3, details of which are omitted here. The narrow electrode interval Dn is formed from ceramic green sheets which may be formed using screen printing, for example.

The sensor element 1 is configured of the wire electrodes 3*a* and 4*a* and the leading electrodes 3*b* and 4*b*, the terminal electrodes 31 and 41, the heater electrode 6*a*, the leading electrode 6*b*, and the terminal electrode 61 and 62, for example, on the ceramic green sheets 2*a* to 2*c*. The abovementioned elements may also be laminated as shown in either FIG. 3 or FIG. 4, and sintered for unification thereof. More specifically, the insulating body 2 consists of an insulation layer which includes the first insulation layer 21 to the third insulation layer 23. The third insulation layer 23 is arranged to cover the outer-side of the pair of detection electrodes 3 and 4 in the element thickness direction Z of the detecting portion 11. The first to third insulation layer 21 to 23 have a constant width in the element width direction Y of the detecting portion 11, which is sufficiently larger than a wire length of the wire electrodes 3*a* and 4*a*. The first to third insulation layers 21 to 23 are crimped to each other on both sides of the pair of wire electrodes 3*a* and 4*a*, without going through the wire electrodes 3*a* and 4*a*. In this way, the insulation layers (specifically, the first to third insulation layers 21 to 23) incorporate the outer-side of the pair of detection electrodes 3 and 4 which are exposed on the surface at the front end surface of the insulating body 2 which forms the detecting portion 11. As a result, detachment of the detection electrodes 3 and 4 is prevented.

A layer thickness of the third insulation layer 23 is usually formed to be thicker than the thickness of the first insulation layer 21, for example, and the insulation layer 23 is formed to have a layer thickness which is the same as or greater than the second insulation layer 22. The third insulation layer 23 is preferably a thick layer, as a prevention measure against detachment of the detection electrodes 3 and 4, to secure insulation properties of the insulation layers, and maintain constant electrode intervals. However, in this regard, since a region in which the detection electrodes 3 and 4 may be formed becomes narrow, the layer thickness of the third insulation layer 23 is preferably in a range of three times greater or less than the thickness of the second insulation layer 22.

When the third insulation layer 23 on the top layer is too thin, a stiffness thereof is reduced, and detachment of the third layer 23 may occur, therefore, the third insulation layer 23 is formed to be thicker than the first insulation layer 21. However, if the third insulation layer 23 is formed to have a thickness which is excessively thick, a size of the insulating body and cost thereof increases, therefore, the thickness is desirably three times greater or less than the thickness of the second insulation layer 22.

Figure 5:
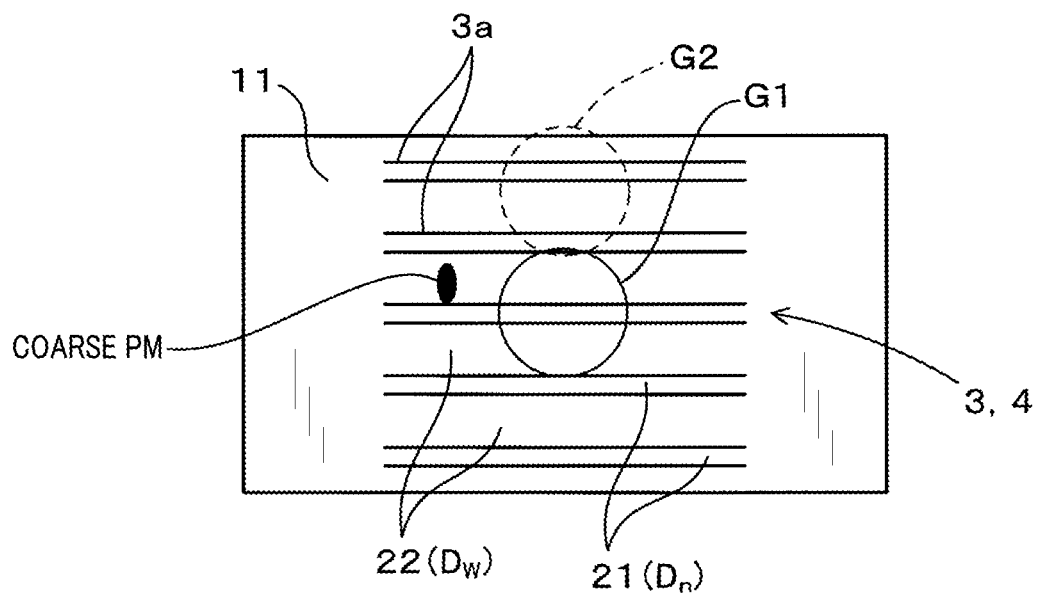
FIG. 5 is a schematic configuration showing a reference example of a disposed position of detection electrodes of detecting portion of the sensor element according to the first embodiment.

As a result, the detecting portion 11 is configured of the pair of wire electrodes 3*a* and 4*a* opposed to each other with the first insulation layer 21 intervened therebetween, and the pair of wire electrodes 3*a* and 4*a* opposed to each other with the second insulation layer intervened therebetween, each of the above mention pair of wire electrodes alternately arranged in the element thickness direction Z, at the front end surface of the insulating body 2, as shown in the reference example in FIG. 5. At this point, the first insulation layer 21 is positioned in a gas flow position G1 in the center part of the detecting portion 11, and the first insulation layer 21 and the second insulation layer 22 are preferably arranged symmetrically, on both sides thereof (specifically, on a respective upper-side and lower-side thereof). The disposed position of the first insulation layer 21 and the second insulation layer 22 is exemplified in FIG. 5 and also exemplified in FIG. 6 to FIG. 8, which will be described hereinafter.

The detecting portion 11 is provided with the first insulation layer 21 in the center part. The first insulation layer 21 in the center part is intervened between the second insulation layer 22 and the first insulation layer 21 alternately disposed in this order on both sides thereof, as shown in FIG. 5. For example, four second insulation layers 22 are disposed between five first insulation layers 21, and the first insulation layer 21 disposed on the most outer-side thereof is positioned near to an edge section of the detecting portion 11 in the Z direction. In this way, by arranging the pair of wire electrodes 3a and 4a having the narrow electrode interval Dn in the center of the detecting portion 11 which corresponds to the gas area position G1 of combustion exhaust gas, minute particulate matter which flows via the gas inlet/outlet holes 5a and 5b to the detection electrodes is promptly detected, thus the sensitivity of the sensor is enhanced. Additionally, by providing the pair electrode wires 3a and 4a which have the wide electrode interval Dw arranged in plurality and increasing a detection area, for example, particulate matter may be detected, even if the combustion gas flow is misaligned with the center of the detecting portion 11 and is guided to flow to the gas area G2 position. As a result, particulate matter is further captured between the wire electrodes 3a and 4a disposed on the outer-side thereof, even in a case of the cover body 5 having variable dimensions or an assembly of the cover body 2 on sensor element 1 varies and the position of the gas flow area is misaligned from the center of the detecting portion 11. As a further result, a decrease of the sensitivity of the sensor is avoided. A difference in sensitivity between sensors is also prevented, thus a detection precision is enhanced.

Additionally, since the pair of wire electrodes 3a and 3b of the wide electrode interval Dw and the pair of wire electrodes 3a and 3b of the narrow electrode interval are alternately disposed, a wide area of the electrode interval is increased. For example, even if particulate matter accumulated in the exhaust pipe detaches therefrom and flows as coarse PM particles (that is, coarse PM shown in the figures), a probability of conduction between the wire electrodes 3a and 4a is decreased, since a wide section between the electrodes is formed. As a result, an acute increase of the sensor output due to coarse PM particles is suppressed, and precision of detection is enhanced.

Figure 9:
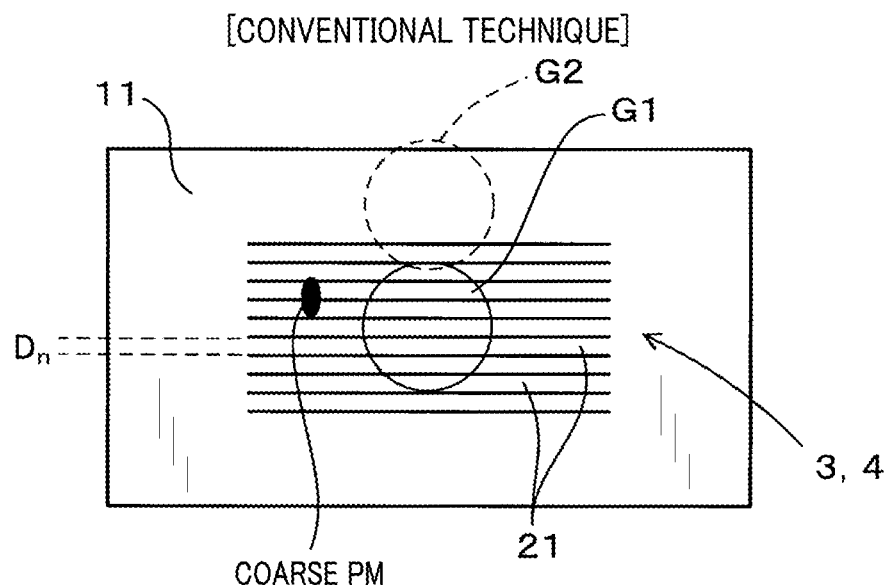
FIG. 9 is a diagram of a schematic configuration showing an example of a disposed position of detection electrodes of a detecting portion according to a conventional sensor element.

In contrast, a conventional sensor element shown in FIG. 9 is provided with electrode intervals between the detection electrodes 3 and 4 which have a constant electrode intervals, and the wire electrodes 3a and 4a arranged in parallel between a plurality of first insulation layers 21 in a center part of a detecting portion 11. In this way, by providing only narrow electrode intervals Dn, the sensitivity of a sensor is increased, however, a detection area of the detecting portion 11 is decreased and a surrounding area without the detection electrodes 3 and 4 disposed thereon is also increased. As a result, if the gas flow position G1 is misaligned with the center part thereof, a large part of the peripheral gas flow area G2 will then be out of range with the detection electrodes 3 and 4, thus the difference in sensitivity between sensors will increase and the detection precision also decrease. When a coarse PM particle which is larger than the electrode interval Dn (specifically, the coarse PM particle shown in the figure) adheres to the detection electrodes 3 and 4, the output of the sensor will sharply increase. Therefore, when the detection sensor is used as a DPF malfunction diagnosis apparatus, there is a concern that a normal DPF may be determined to be abnormal.

The narrow electrode interval Dn, specifically the layer thickness of the first insulation layer of the detecting portion 11 is usually set in a range of 1 μm to 60 μm, and preferably between 5 μm to 60 μm. It has been confirmed that particulate matter size is generally distributed, for example, in a range of 10 nm to 100 nm, with a center particle diameter of approximately 40 nm. In order to promptly detect the above mentioned particulate matter, the narrower the electrode interval Dn is configured to be the better. However, if the layer thickness of the first insulation layer 21 is thin, time and labor needed to manufacture the detecting portion 11 with a desired dimensional precision, and there is a concern of the frequency of an acutely increased output due to adherence of the coarse PM particles also increasing.

In contrast, the wide electrode interval Dw, specifically the layer thickness of the second insulation layer 22 is usually set in a range of 20 μm to 300 μm, and more preferably in a range of 20 μm to 100 μm. It is estimated that a size of the coarse PM particles is usually in a range of several μm to 100 μm, provided with a center particle diameter of approximately 20 μm. Therefore, by providing the electrode interval Dw at 20 μm or more, a preventive effect of the acute increased output due to the adherence of the coarse PM particles is enhanced. As described above, the layer thickness of the third insulation layer 23 is greater than a layer thickness of the first insulation layer 21 and three times or less than the thickness of the second layer 22, (specifically a thickness of more than 1 μm and 900 μm or less) which is preferably set in a range of 100 μm to 400 μm.

As the sensor 11 is provided with the detection electrodes 3 and 4 arranged in a larger region, the sensitivity of the sensor is increased and a response thereof may also be enhanced. Specifically, when the element width of the sensor element 1 (that is, a length of the element width direction Y of the front end surface being the detecting portion 11) is in a range of 3 mm to 5 mm, for example, a width of the detection electrodes 3 and 4 (that is, a linear length of the wire electrodes 3a and 4a of the element width direction Y) is set in a range of 2 mm to 4 mm, for example.

At this point, if a length of the first to third insulation layers 21 to 23 positioned on the outer-side of the wire electrodes 3a and 4a is in a range of 0.4 mm to 1 mm in total for both ends, in the element width direction Y (specifically, between 0.2 mm to 0.5 mm for one end) a crimping performance between the insulation layers is secured, and detachment, for example, thereof may also be prevented. The element thickness (that is, a length of the element thickness in the Z direction of the front end surface which is the detecting portion 11) is in a range of 1 mm to 3 mm, for example, and a desired number of the pairs of the detection electrode 3 and 4 may be disposed with a desired interval therebetween, in the element thickness direction Z, with a position and layer thickness of the first insulation layer 21 or the second insulation 22 which is preferably set in the range described hereinabove.

Figure 6:
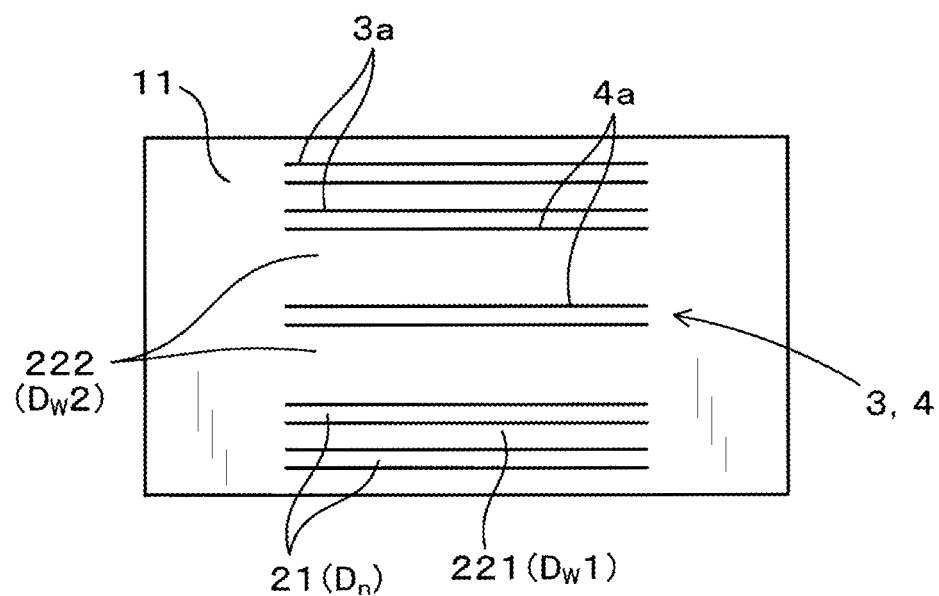
FIG. 6 is a schematic configuration showing an example of the disposed position of the detection electrodes of the detecting portion of the sensor element according to the first embodiment.
Figure 7:
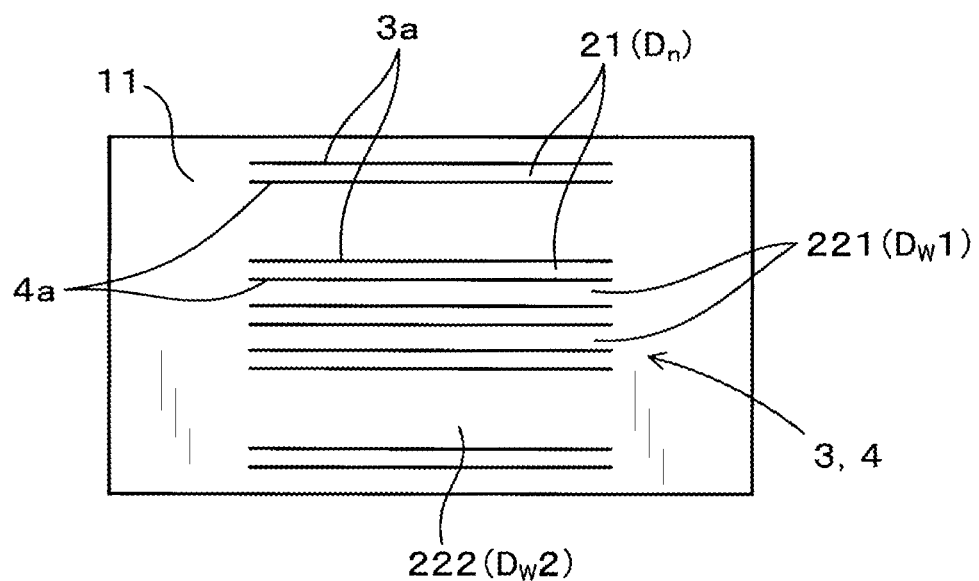
FIG. 7 is a diagram of a schematic configuration showing an example of the disposed position of the detection electrodes of the detecting portion of the sensor element according to the first embodiment.

The detecting portion 11 may be configured with the second insulation layer 22 which has of a plurality of insulation layers 221 and 222 combined, which have different layer thicknesses. The second insulation 22 forms the electrode interval Dw which is wider than the first insulation layer 21, as shown in FIG. 6 and FIG. 7. In providing the plurality of insulation layers 221 and 222, electrode intervals Dw1 and Dw2 formed between the wire electrodes 3a and 4a are both configured wider than the electrode interval Dn, and may be appropriately set within the same range as the electrode interval Dw of the second insulation layer 22. At this point, for example, the electrode interval Dw2 of the insulation layer 222 is formed wider than the electrode interval Dw1 of the insulation layer 221. The electrode interval Dw1 of the insulation layer 221 is formed narrower than the electrode interval Dn, thus the detection area is configured the same as the area of the detecting portion 11 shown in FIG. 5 (Specifically, Dn<Dw1<Dw<Dw2).

In FIG. 6, the insulation layer 222 providing the electrode interval Dw2 which is wider than the electrode interval Dw is arranged on both sides of the first insulation layer 21 of the center part, between the wire electrodes 3a and 4a. The insulation layer 221 is arranged on an outer-side of the insulation layer 222 via the first insulation layer 21. In this way, as the insulation layer 222 of the wider electrode interval Dw2 is arranged near to the center first insulation layer 21, the increased output due to the adhesion of the coarse PM particles may be suppressed, for example, when coarse PM particles easily flow to the detecting portion 11. If the PM detection sensor is adapted as a malfunction detection system, an effect of preventing erroneous detection is enhanced.

As shown in FIG. 7, the insulation layer 221 which has a smaller thickness may be arranged on both sides with the first insulation layer 21 provided in the center, intervened therebetween, on the detecting portion 11. The insulation layer 222 which has a greater thickness is disposed on an outer-side of the insulation layer 221 via the first insulation layer 21. For example, when a configuration is such that the gas flow position G1 is easily misaligned from the center part due to an effect of the varying dimension of the cover body 5, for example, the insulation layer 221 which has a comparatively narrow electrode interval Dw1 is positioned near to the center first insulation layer 21, and the pairs of wire electrodes 3a and 4a gathered so that the sensitivity of the sensor may be enhanced.

Figure 8:
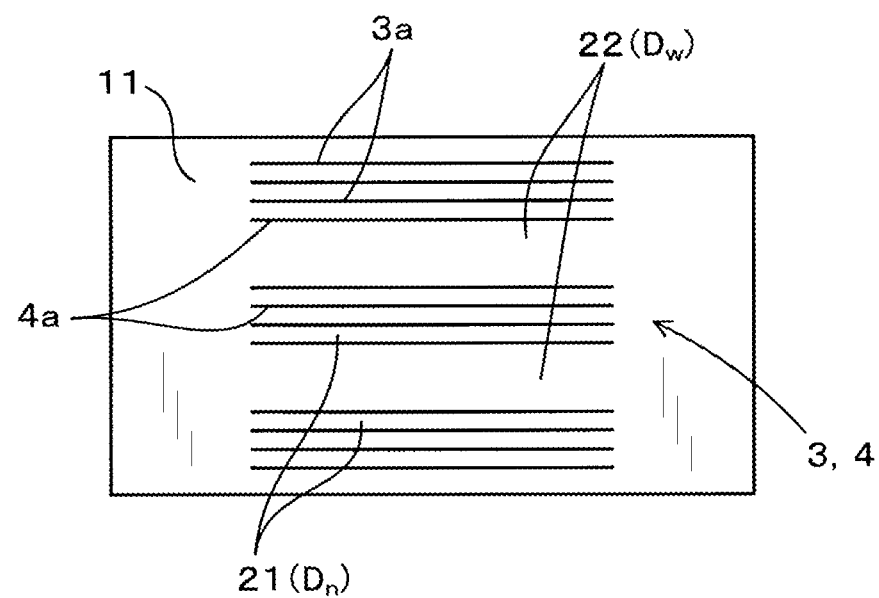
FIG. 8 is a diagram of a schematic configuration showing an example of the disposed position of the detection electrodes of the detecting portion of the sensor element according to the first embodiment.

Additionally, as shown in FIG. 8, in providing the plurality of first insulation layers 21 disposed in both the center part and peripheral area of the sensor 11, the number of the wire electrodes 3a and 4a mounted may be increased. The second insulation layer 22 is disposed in the center part and the peripheral area thereof. The wire electrodes 3a and 4a are alternately arranged with the first insulation layer 21 intervened therebetween at the center part and the peripheral areas thereof, and each the second insulation layers 22 is disposed in between the three layers of the first insulation layers 21. Since the pair of wire electrodes 3a and 4a of the electrode interval Dn are formed in pluralities at the center part and the peripheral area thereof, a difference in sensitivity levels between sensors may be prevented, even when the gas area position is easily misaligned with the center part thereof. Additionally, since the pair of wire electrodes 3a and 4a of the electrode interval Dw are also formed therebetween, the decrease in the sensitivity of the sensor may be suppressed, even when coarse PM particles flow into the detecting portion 11.

(Experiment 1)

The sensor element 1 shown in FIG. 5 to FIG. 9 were manufactured as follows. The sensor element 1 was evaluated using a diesel engine bench test machine, and a relation of a disposed position of the electrodes of the sensor 11 and the sensor output was investigated. The sensor element 1 had an element width of 4 mm, an element thickness of 1.6 mm and an electrode width of 3.2 mm. Alumina green sheets were produced with an adjusted thickness and used as the ceramic green sheets 2a to 2c. Alumina green sheets were obtained by adding a solvent, for example, ethanol, and a binder solvent to alumina powder to form a slurry. The slurry was then formed into a sheet shape using a known Doctor Blade method and dried thereafter. The obtained alumina green sheets were then cut into a predetermined size, and the wire electrodes 3a and 4a which are the detection electrodes 3 and 4, and the leading electrodes 3b and 4b respectively formed at predetermined positions using screen printing method, for example. In the same manner, the heater electrodes 6a and leading electrode 6b was also formed at respective predetermined positions on the alumina green sheets which is the heater 6, using screen printing, for example. Additionally, the terminal electrodes 31, 41, 61 and 62 were formed on the alumina green sheet disposed on either one of the top layer or the bottom layer of the sensor element.

The alumina green sheets were laminated in a predetermined order, crimped by pressing using uniaxial pressing or cold isostatic pressing method, for example, after which they were subjected to delipidation and then sintered (for example, at 1450° C. for 2 hours). Thereafter, the detection electrodes 3 and 4 of the detecting portion 11 were exposed by sanding the surface of the insulating body 2. Additionally, the leading electrodes 3b and 4b exposed to a side surface of the insulating body 2 were connected to respective terminal electrodes 31 and 41 via a conductive section using conductive paste, for example. In the same manner, the leading electrode 6b of the heater 6 was connected to the terminal electrodes 61 and 62 and the sensor element 1 was obtained.

At this point, the thickness of the alumina green sheets forming the respective first insulation layer 21 and the second insulation layer 22 was adjusted, and the sensor element 1 provided with the detecting portion 11 shown in FIG. 5 to FIG. 8, was produced by changing a disposed position of the wire electrodes 3a and 4a and a laminated order of the insulation layers. Each of sensor elements 1 was referred to as a respective sensor elements S1 to S4. A sensor element 1 provided with a conventional detecting portion 11 shown in FIG. 9 referred to as sample 0, was also produced for comparison.

The sensor element 1 obtained was accommodated inside the cylindrical housing H, the cover body 5 was assembled thereto and the result configuration given as the particulate matter detection sensor S. A DPF which was opened so that the particulate matter in combustion gas slipped through the DPF was mounted on an exhaust pipe of a diesel engine, and the particulate matter detection sensor S assembled to a wall of the exhaust pipe in a position which was 1000 mm downstream of the DPF. The particulate matter detection sensor S was mounted in order to be exposed to the combustion exhaust gas which was the measuring gas. The front end-side of the sensor element protected by the cover body 5 was inserted and positioned inside the exhaust pipe. A radius of the exhaust pipe was $\phi$ 55 mm and the combustion gas was introduced into the exhaust pipe at a flow rate 40 m/s, a PM concentration 5 mg/m$^3$ and a temperature of 200° C. A predetermined capturing voltage was applied between the detection electrodes 3 and 4 of the sensor element 1 and the particulate matter that passed down stream of the DPF filter was detected. A probability of increased output which occurred as a result of the coarse PM particles and a start-up time of the sensor output was measured.

Figure 10:
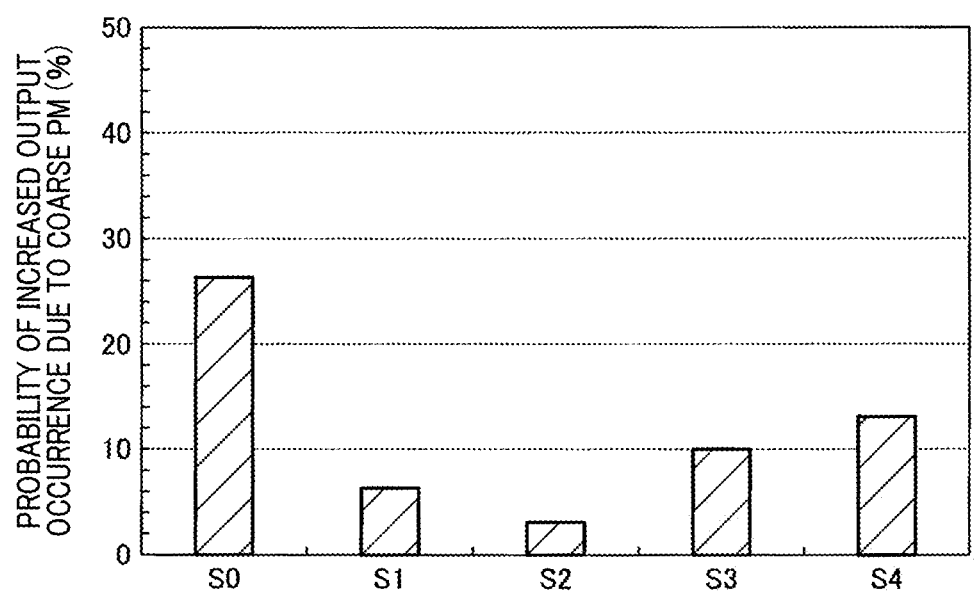
FIG. 10 is a diagram showing a relation between the disposed position of the detection electrodes of the detecting portion of the sensor element and a probability of output increase occurring due to coarse PM particles.
Figure 11:
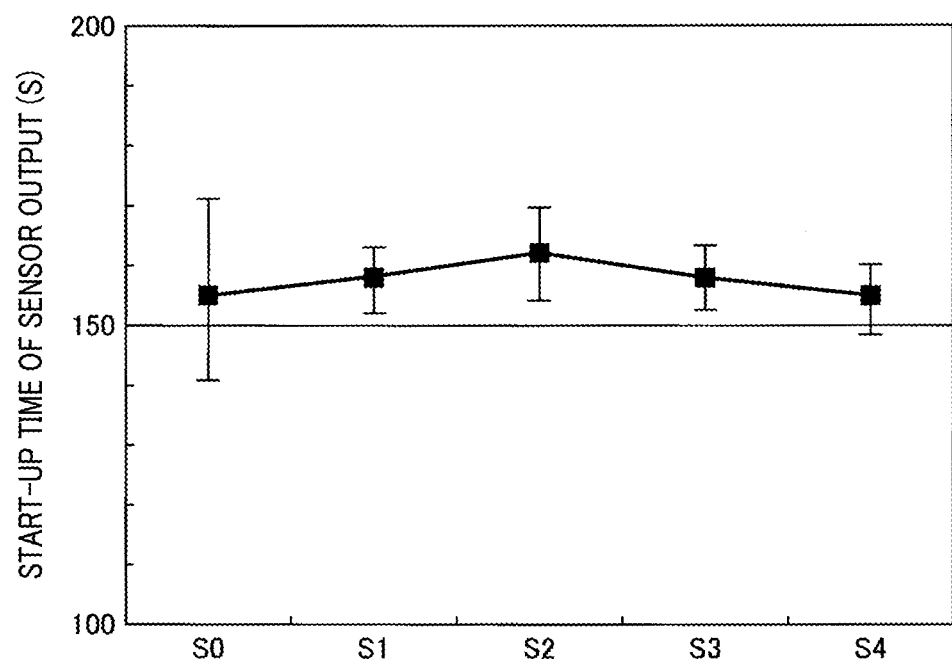
FIG. 11 is a diagram showing a relation between the disposed position of the detection electrodes of the detecting portion of the sensor element and a start-up time of the sensor output.

Results are shown in FIG. 10 and FIG. 11. The probability of the increased output occurrence due to the coarse PM particles was calculated from an occurrence rate of a number of times in which the output of the sensor was acutely increased due to the adherence of coarse particulate matter, using the particulate matter detection sensor S, when the sensor output start-up time was measured a predetermined number of times (for example 30 times) described later in detail. Additionally, the start-up time of the sensor output is a time from when the capturing voltage is applied until a predetermined sensor output (for example, 15 µA) is reached, in which an average value and a difference thereof is calculated (for example, when performed 30 times). The start-up time is specifically after the electricity is supplied to the heater 6, to regenerate the sensor 1 performed by removing particulate matter adhered to the sensor element.

As shown in FIG. 10 and FIG. 11, the probability of the increased output occurring due to the coarse PM particles exceeded 25% and the start-up time of the sensor output had a high variance for the sample 0 which was configured with constant electrode intervals Dn between the detection electrodes 3 and 4 of the detecting portion 11. In contrast, the probability of the increased output was lower than 15% and the start-up time had a low variance for any one of the samples S1 to S4. In particular, the probability of the increased output was largely decreased to 10% or less for the samples S1 to S3 configured with the wide electrode intervals Dw, Dw2 and Dw1, on both sides of the electrode interval Dn of the wire electrodes 3a and 4a provided in the center part of the detecting portion 11. It was found that the wider the electrode intervals Dw, Dw1 and Dw2 were configured (specifically, Dw1<Dw<Dw2) the lower the effect of the coarse particulate matter was. In contrast, the narrower the electrodes intervals Dw, Dw1 and Dw2 were configured, the lower the variance was of the sensor output time, as a result, a difference in the sensitivity between sensors was also small. The sample 4 which is provided with the plurality of wire electrode pairs 3a and 4a of the electrode interval Dn in the center of the detecting portion 11 had the shortest sensor startup time and a high sensitivity.

As a result, the disposed position of the detection electrodes 3 and 4 of the detecting portion 11 may be suitably adjusted according to a sensor needs and usage. For example, in an environment where the effect of coarse PM particles is comparatively large, for example, electrodes which have a disposed arrangement of sample 1 or sample 2 is selected. Specifically, the disposed arrangement of the electrodes which suppresses a changing output and has a small variance in sensitivity of the sensor as shown in FIG. 5 (specifically, sample 1) or which elicits a high suppression effect for an output variation, as shown in FIG. 6 (for example, sample S2) is selected. In an environment where the effect of coarse PM particles is comparatively small, electrodes which have a disposed arrangement as in sample S3 and sample S4 are selected. Specifically, the disposed arrangement of the electrodes (specifically sample S3) shown in FIG. 7 which can both decrease varying sensitivity and suppress the changing output of the sensor or the disposed arrangement of the electrodes (specifically sample 4) which further enhances the sensitivity of the sensor as shown in FIG. 8 may be selected.

Second Embodiment

Figure 12:
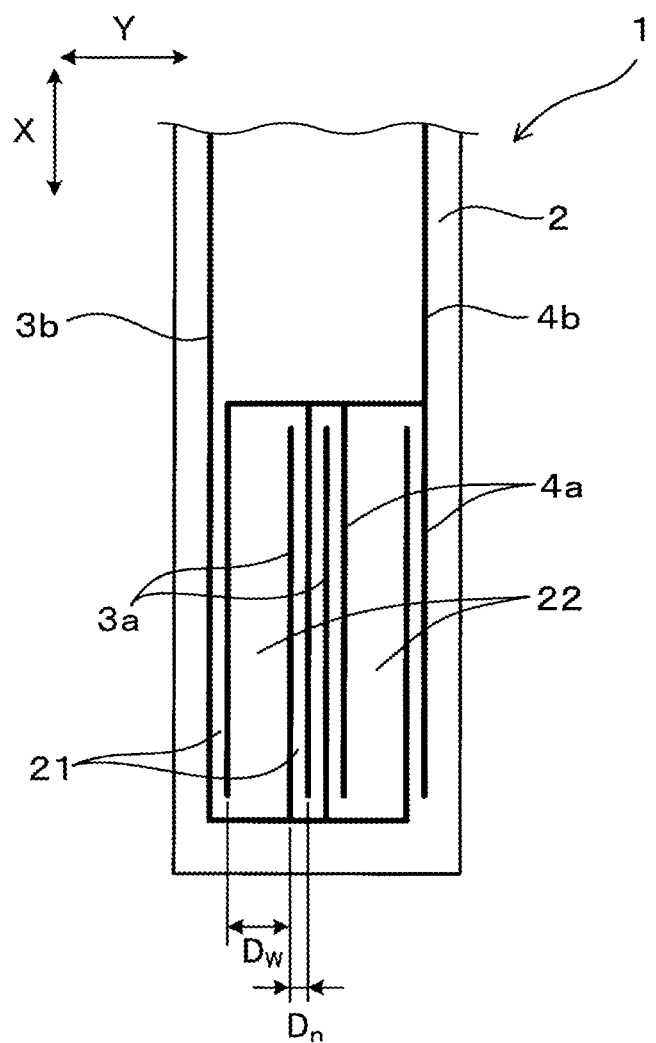
FIG. 12 is an enlarged diagram of a major part showing a schematic configuration of the sensor element of the particulate matter detection sensor according to a second embodiment.
Figure 13:
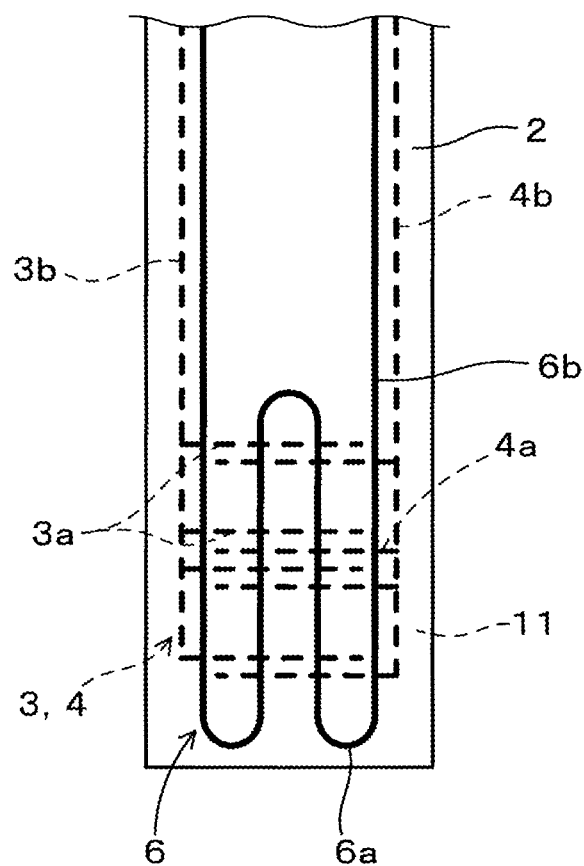
FIG. 13 is an enlarged diagram of an important part of a diagram showing another example of a relation between the disposed position of the detection electrodes of the detecting portion of the sensor element and a heater position, according to the second embodiment.

In the first embodiment, the front-end surface of the laminate-type sensor 1 is the detecting portion 11 configured with the plurality of the wire electrodes 3a and 4a embedded in the insulating body 2. The pair of detection electrodes 3 and 4 may also be formed on a surface other than the front-end surface of the insulating body 2, as shown in FIG. 12 and FIG. 13 for a second embodiment. A basic configuration of the particulate matter detection sensor S according to the second embodiment is the same as the first embodiment, therefore the difference between the embodiments is mainly described herein below. The sensor element 1 is provided with a flat shape insulating body 2, and the pair of detection electrodes 3 and 4 disposed as the detecting portion 11 on a front-end surface of a plate surface. The detection electrodes 3 and 4 are connected to a terminal electrode, which is not shown in the figures, by the leading electrodes 3b and 4b, formed in the element length direction X on the surface of the insulating body 2. Each of the plurality of wire electrodes 3a and 4a are a comb shaped electrode connected to one end-side thereof. Each of the wire electrodes 3a and 3b of the detection electrodes 3 and 4, and the leading electrodes 3b and 4b are formed by a known screen printing, for example.

In FIG. 12, the wire electrode 3a electrically connected to the detection electrode 3 which is the positive electrode, and the wire electrode 4a electrically connected to the detection electrode 4 which is the negative electrode are alternately disposed in parallel in the element width direction Y, and the pair of the wire electrodes 3a and 4a which are adjacent to each other are formed in pluralities. The intervals of the adjacent wire electrodes 3a and 4a are provided in an order of the pair of wire electrodes 3a and 4a of the narrow electrode intervals Dn pluralities (for example, three pairs) in a center part of the element width direction Y, and-the pair of wire electrodes 3a and 4a of the wide electrode interval Dw, and the pair of wire electrodes 3a and 4a of the narrow electrode interval Dn disposed on both sides of the pluralities of the wire electrodes 3a and 4a. The first insulation layer 21 is formed between the wire electrodes 3a and 4a of the narrow electrode interval Dn, and the second insulation layer 22 is formed between the wire electrodes 3a and 4a of the wide electrode interval Dw. An electrode length and an electrode width of the wire electrodes 3a and 4a may be appropriately set. It is noted that, in the present embodiment, the element width direction Y is a width direction of the plate surface formed by the detecting portion 11 of the insulating body 2.

In this way, by providing the detection electrodes 3 and 4 as print-formed electrodes, adjustment of the electrode interval Dn and the electrode interval Dw is easily performed. As shown in FIG. 13, a configuration in which the wire electrode 3a electrically connected to the detection electrode 3 which is the positive electrode, and the wire electrode 4a electrically connected to the detection electrode 4 which is the negative electrode are alternately disposed in parallel in the element length direction X on the detecting portion 11, may also be provided. In this configuration, the pair of wire electrodes 3a and 4a of the narrow electrode interval Dn are disposed in pluralities (for example, 3 pairs) in the center part of the element length direction X. Additionally, the pair of wire electrodes 3a and 4a of the wide electrode interval Dw and the pair of wire electrodes 3a and 4a of the narrow electrode interval Dn are disposed in this order on both sides of the center part thereof. The heater 6 is disposed on a side which opposes the detecting portion 11 of the insulating body 2 at the front-end surface thereof. Specifically, the heater 6, in which the heater electrode 6a is disposed, is configured to cover a region formed by the wire electrodes 3a and 4a of the detection electrodes 3 and 4. The heater 6 and the leading electrode 6b are formed using a known screen printing method, for example. The heater 6 may also be combined with the arranged position of the electrodes shown in FIG. 12. In this case, the heater 6 is preferably configured to cover an entire region in which the wire electrodes 3a and 4a are formed.

Figure 14:
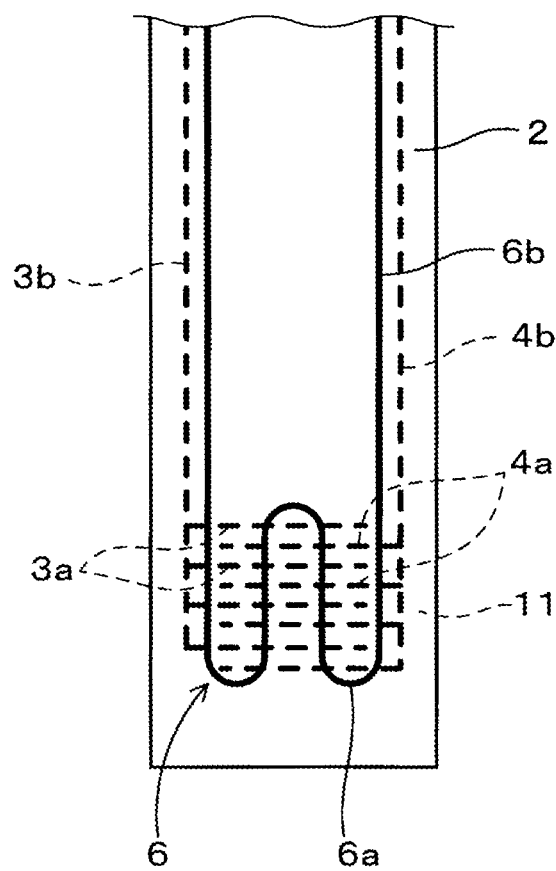
FIG. 14 is an enlarged diagram of an important part of a diagram showing an example of a relation between a disposed position of detection electrodes of a detecting portion according to a conventional sensor and a heater position.

As a result, the detecting portion 11 shown in FIG. 13 has a larger detection area which corresponds to the wire electrodes 3a and 4a, compared to a conventional configuration of the detecting portion 11 which is provided with the detection electrodes 3 and 4 formed with constant electrode intervals, as shown in FIG. 14. Furthermore, the sensitivity of the sensor may be enhanced without increasing the number of electrodes. If the wire electrodes 3a and 4a are disposed to extend in the length direction X of the element, the detection area is easily enlarged without changing the electrode intervals Dn and Dw or the number of electrodes provided, as shown in the detecting portion 11 in FIG. 12.

It is noted that, unless specifically shown, the same symbols for configuring elements described in the first and second embodiments are used hereinafter.

Third Embodiment

Figure 15:
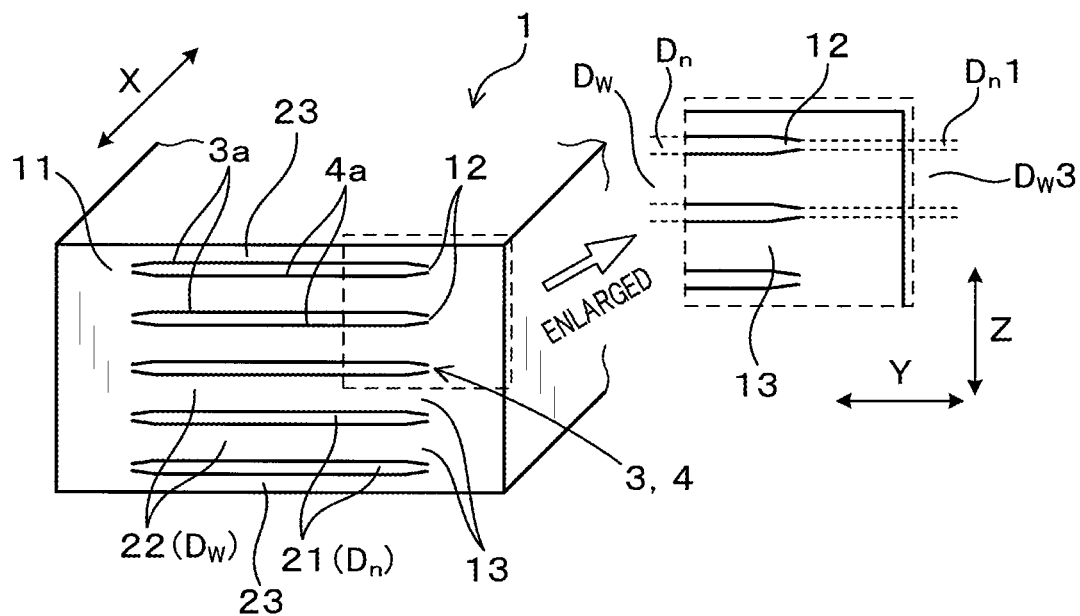
FIG. 15 is an enlarged diagram of a major part showing a schematic configuration of the sensor element of the particulate matter detection sensor according to a third embodiment.

In the first and the second embodiments, the wire electrodes 3a and 4a which form the detection electrodes 3 and 4 of the sensor 1 are configured so that each pair of electrodes are provided with constant wide electrode intervals Dw, Dw2 and Dw1 or narrow electrode intervals Dn, however, the disposed position of the electrodes (specifically, the length direction of the wire electrodes 3a and 4a) may also be changed to the element width direction Y. The laminate formed sensor element 1 shown in FIG. 15 is an example of configuration which may be adapted for a third embodiment. A basic structure of the detecting portion 11 is the same as the first embodiment shown in FIG. 5. A difference (between the two configurations) will mainly be described, hereafter.

As shown FIG. 15, the detecting portion 11 provided on the front end surface of the sensor 1 has the pair of wire electrodes 3a and 4a of the wide electrode interval Dw and the pair of wire electrodes 3a and 4a of the narrow electrode interval Dn alternately positioned. The pair of wire electrodes 3a and 4a of the narrow electrode interval Dn are disposed in the center part of the detecting portion 11, and the pair of electrodes of the wide electrode interval Dw in addition to the pair of wire electrodes 3a and 4a of the narrow electrode interval are symmetrically disposed in this order on both sides thereof, in the element thickness direction Z. Additionally, the pair of wire electrodes 3a and 4a of the narrow electrode interval Dn are provided with a small width section 12 on both ends, in the element width direction Y. The small width section 12 has an electrode interval Dn1 which is narrower than other parts thereof.

Figure 16:
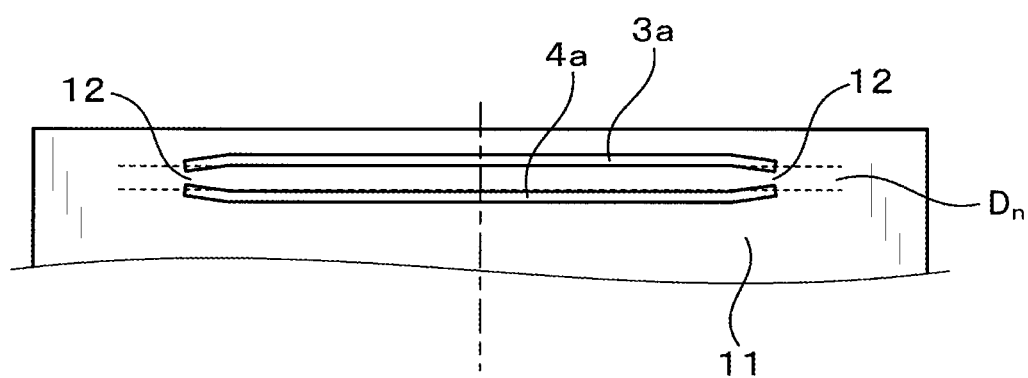
FIG. 16 is an enlarged diagram of a part of the detecting portion of the sensor element according to the third embodiment.

Specifically, a main part of each pair of narrow electrode intervals Dn is arranged to have a constant narrow electrode interval Dn, from the center part of the element width direction Y to both end ends thereof, among the wire electrodes 3a and 4a arranged on the detecting portion 11. Both tip ends which continue from the main part are provided to face both respective ends, so that the interval of opposing wire electrodes 3a and 4a gradually becomes narrow to form a taper shaped electrode arrangement, and the small width section 12 is formed as a narrowest interval part at both tip ends. In FIG. 15, one side of the tip end is shown enlarged. Additionally, when a virtual line (specifically, broken line in FIG. 16) which is extended from opposed ends of the wire electrode 3a and 4a is set, edges which oppose the both tip ends which form the small interval section 12 are each positioned on the inner side thereof, pass the virtual line.

Among the wire electrodes 3a and 4a of the detecting portion 11, a large width section 13 is formed on both ends of each pair of the wide electrode intervals Dw which are adjacent to the narrow interval Dn. The large width section 13 of the wide electrode interval Dw3 which is wider than other sections thereof is thus formed. That is, each pair of the wide electrode intervals Dw has a major part from the center part of the element width direction Y to both ends thereof formed as a constant wide electrode interval Dw. Both tip ends provided to continue from the main part thereof are configured so that the interval between the opposed wire electrodes 3a and 4a gradually widens to form a taper shaped electrode disposed arrangement, and the large width section 12 formed on the both ends thereof.

The sensor element 1 described above has the pair of wire electrodes 3a and 4a of the narrow electrode interval Dn which is configured with the small width section 12 being further narrowed on the both ends thereof. As a result, the small width sections 12 can detect smaller particles. Additionally, since the sensor element 1 is also provided with the wide width section 13 adjacent to the small width section 12, an effect of suppression of a sudden increase of the sensor output due to the coarse particles is enhanced.

Figure 17:
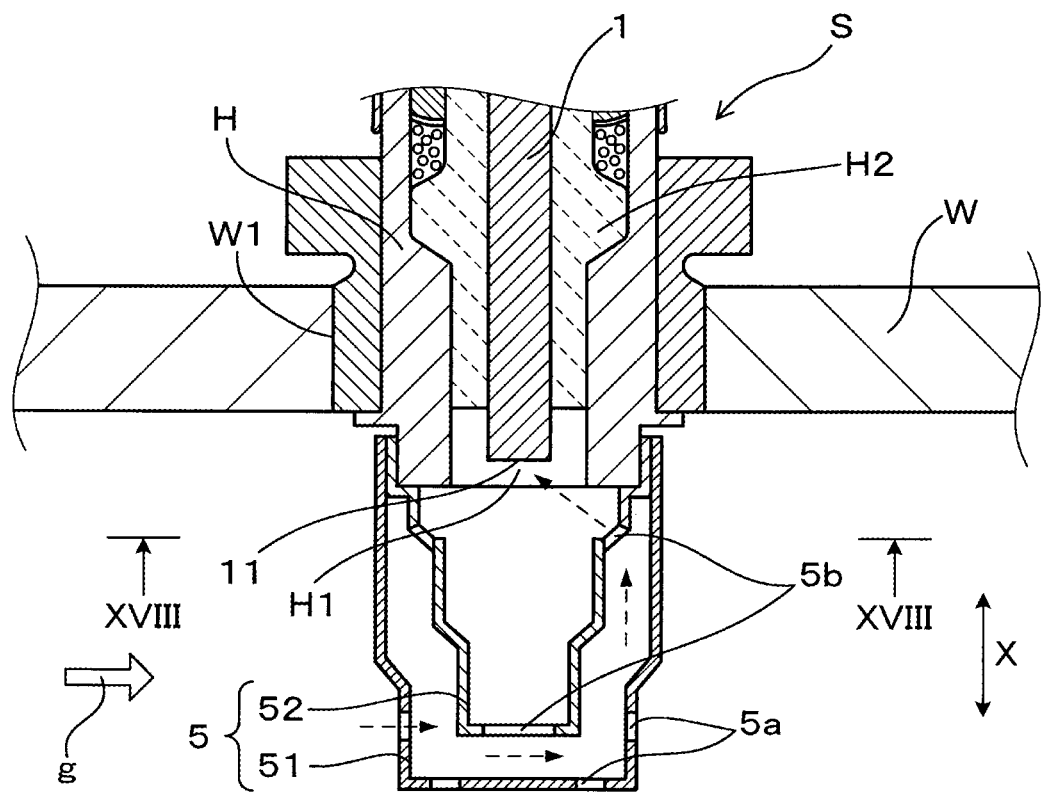
FIG. 17 is a cross sectional view in the axial direction showing a schematic configuration of the particulate matter detection sensor according to the third embodiment.
Figure 18:
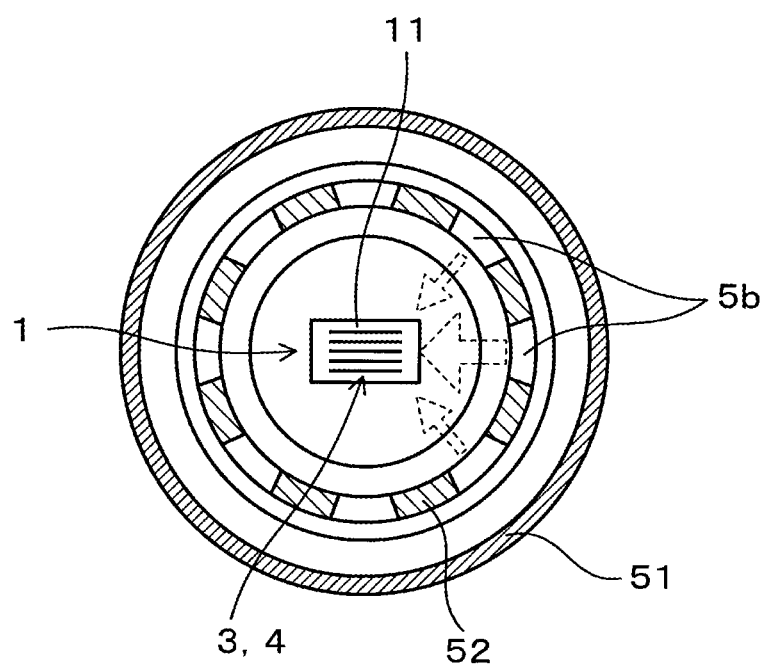
FIG. 18 is a cross sectional diagram across a line XVIII-XVIII of FIG. 17, showing a cross sectional diagram in a radial direction of a schematic configuration of the particulate matter detection sensor according to the third embodiment.

As shown in FIG. 17, the particulate matter sensor S provided with the sensor element 1 described above has the cylindrical housing H which is mounted to the wall W of the exhaust pipe, and the double container shaped cover 5 surrounding an outer circumference of the sensor element 1, configured in the same way as the particulate matter detection sensor S according to the first embodiment, shown in FIG. 2. The cover body 5 is configured so that the combustion gas is introduced to the detecting portion 11 of the sensor element 1, via the plurality of gas inlet/outlet holes 5b of the inner cover 52 from the plurality of inlet/outlet-holes 5a of the outer cover 51. The gas inlet/outlet-holes 5b of the inner cover 52 are positioned slightly lower than the front end of the sensor element 1, for example, 8 gas inlet/outlet holes 5b are equally disposed to surround the sensor 11, as shown in FIG. 18.

At this point, according to the flow of combustion gas introduced from the outer cover 51, the combustion gas is introduced from more than one of any of the 8 gas inlet/outlet holes, to an inside of the inner cover 52, and flows along the surface of the detecting portion 11 towards the gas inlet/outlet hole 5b on an opposed side thereof. By positioning of the sensor element 1 so that a direction of the gas flow and the element width direction Y of the detecting portion 11 (specifically, the length direction of the wire electrodes 3a and 4a) are the same, the combustion gas reliably passes through the surface which includes an end of the detecting portion 11 during which time the particulate matter is captured.

Figure 19:
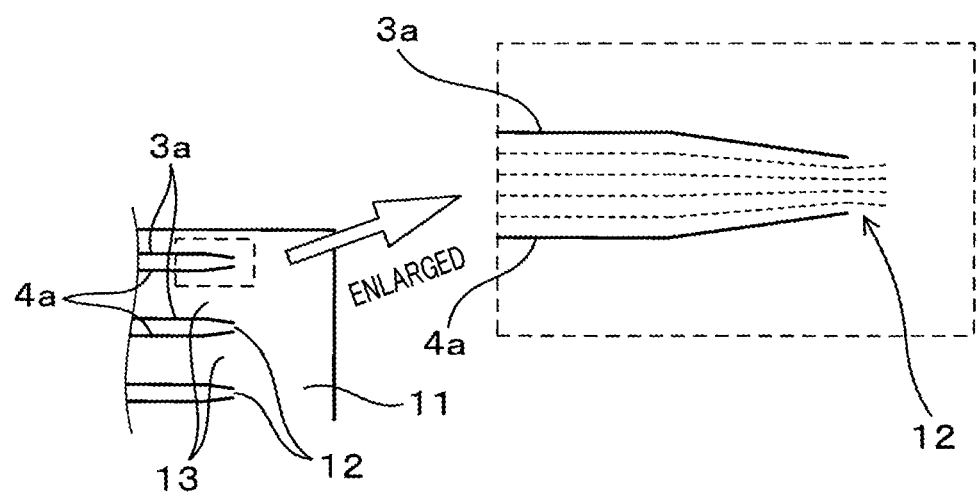
FIG. 19 is enlarged diagram of a part of the detecting portion, descriptively illustrating a working effect of the sensor element, according to the third embodiment.

A mechanism of the above described is shown in FIG. 19. As shown with the broken lines in the enlarged diagram, an interval of equipotential lines is blocked and an electric field occurs at small interval sections 12 provided on both ends of the wire electrodes 3a and 4a of the narrow electrode interval Dn. As a result, a Coulomb's force works and particulate matter is easily gathered at the small interval section 12. As a result, smaller particulate matter can be rapidly captured at side ends of the detecting portion 11. A decrease of the sensitivity due to the wide electrode intervals Dw is thus suppressed, and the detection sensitivity of an entire sensor is enhanced.

Figure 20:
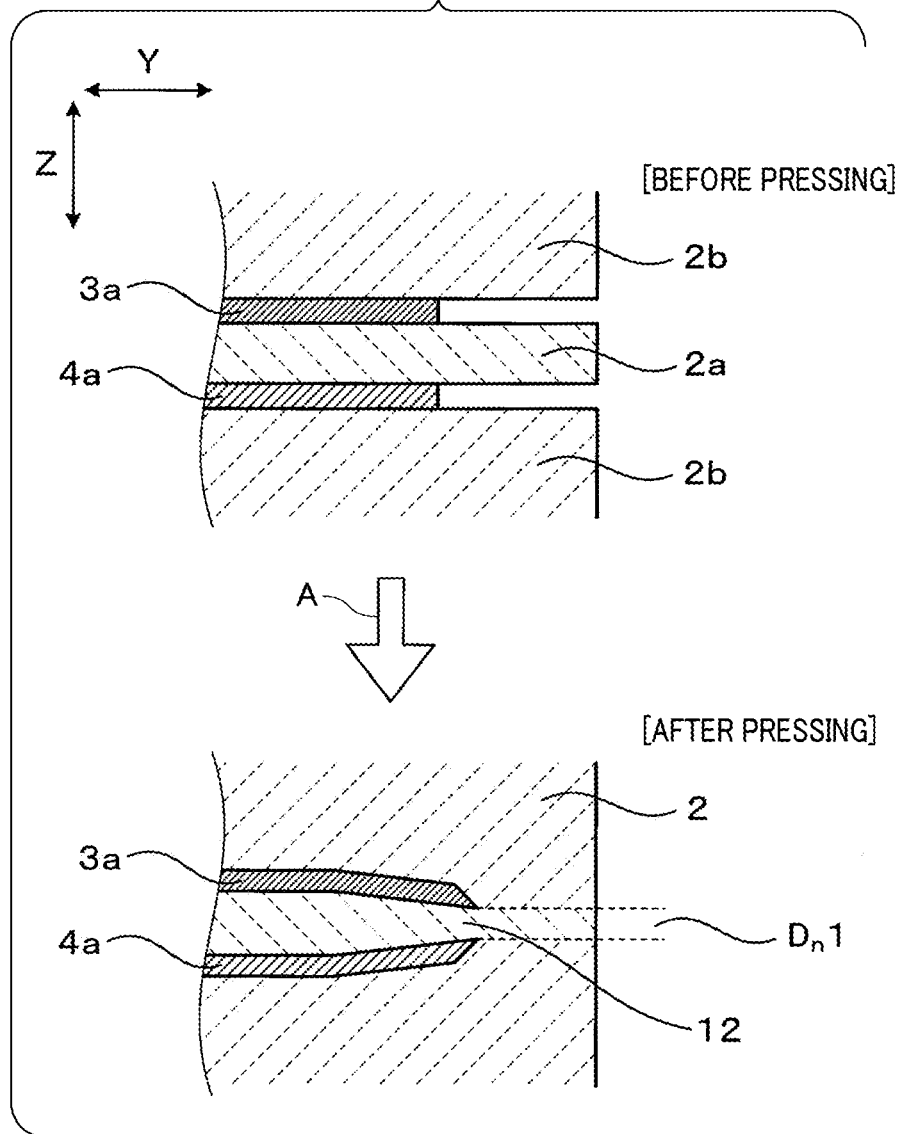
FIG. 20 is a schematic view showing an example of a manufacturing method of a sensor element according to the third embodiment.
Figure 21:
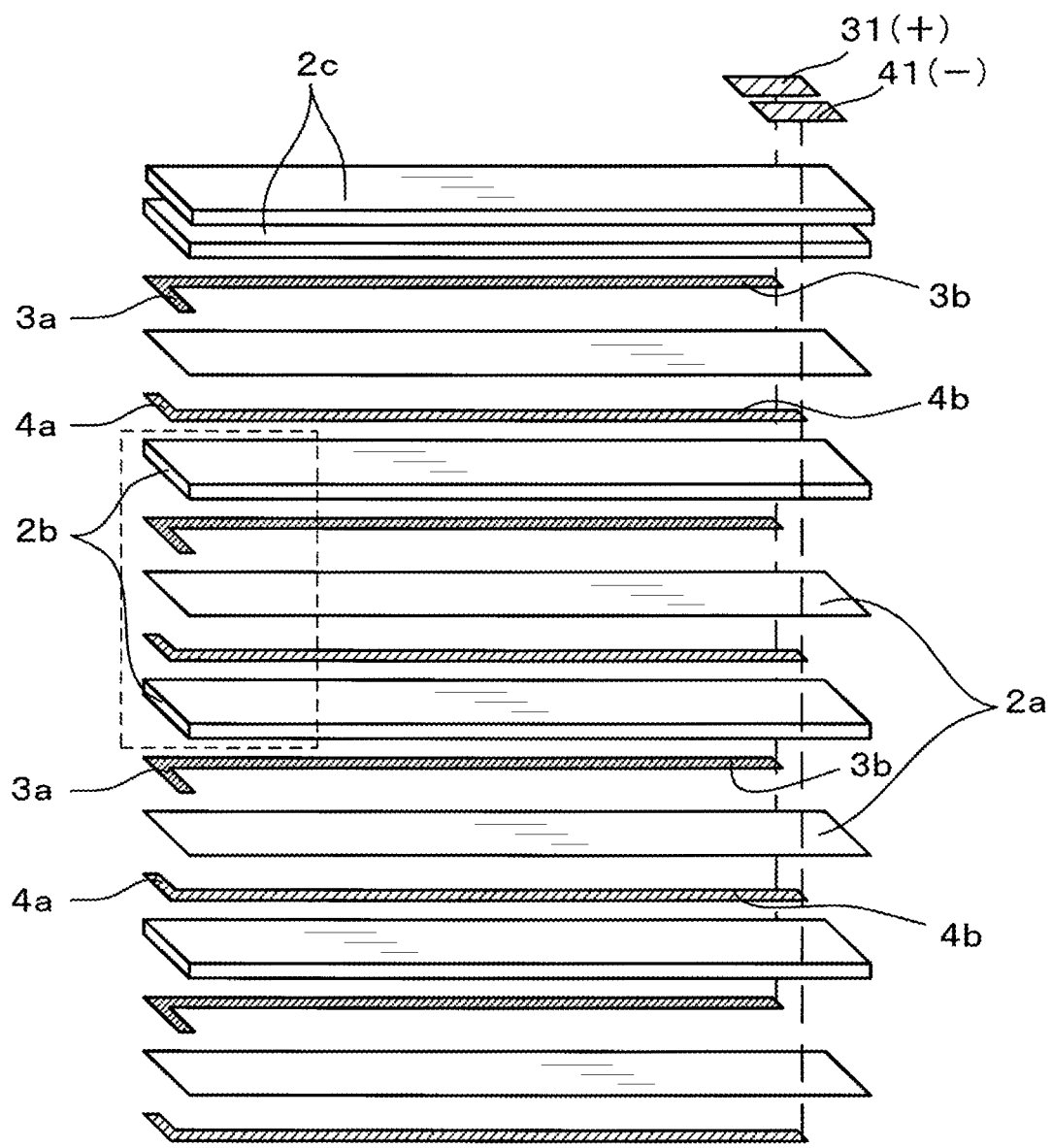
FIG. 21 is an exploded perspective view of the sensor element according to the third embodiment.

When this type of sensor element 1 is manufactured, as was described in the first embodiment, the wire electrodes 3a and 4a may be alternately disposed between the green ceramic sheets 2a to 2c to form the detection electrodes 3 and 4, shown in FIGS. 20 and 21. Specifically, electrodes films which are the respective wire electrodes 3a and 4a are disposed on both a top and bottom surface of the ceramic green sheet 2a, so that the ceramic green sheet 2a which corresponds to the narrow electrode interval Dn is intervened therebetween. The ceramic green sheet 2b which corresponds to the wide electrode interval Dw is further disposed on a top and bottom of the wire electrodes 3a and 4a which are disposed as described above. At this point, on a side of the electrode films which are the wire electrode 3a and 4a (specifically, on an outer-side of the element width direction Y) a gap having a same film thickness as the electrode film is formed between the respective ceramic green sheets 2a and 2b.

Thereafter, as shown with an arrow A in FIG. 20, the entire formed structure is pressed in the element thickness direction Z, so that the green ceramic sheets 2a to 2c are pressed with the electrode films which are the wire electrodes 3a and 4a intervened therebetween, to be unified into one. During this process, a main part of the electrode films which are the wire electrodes 3a and 4a are absorbed into adjacent ceramic green sheets 2a and 2b. In contrast, since the side of the wire electrodes 3a and 4a are not absorbed between the ceramic green sheets 2a and 2b, a density of the sides of the wire electrodes 3a and 4a remains low, compared to other parts. As are result, if further pressing is applied thereto, the ceramic green sheets 2a and 2b break more easily, and the opposed ends deform to become closer to each other, forming the small width section 12 on the both ends of the wire electrodes 3a and 4a. The large width section 13 is also formed on an outside of the small width section 12, which is omitted from the figure.

Fourth Embodiment

Figure 22:
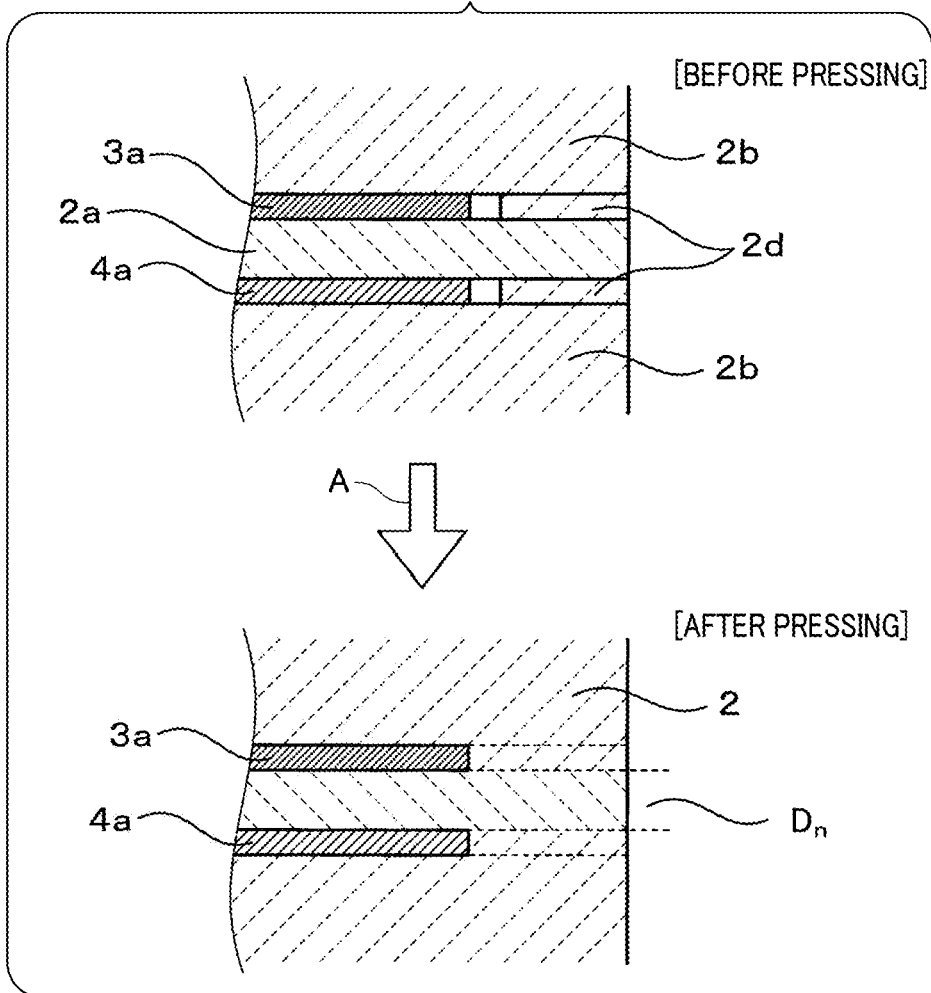
FIG. 22 is a schematic view showing a configuration and an example of a manufacturing method of the sensor element according to a fourth embodiment.

As a fourth embodiment, when a configuration is such that the small width section 12 is not formed, a ceramic green sheet 2d which has the same film thickness may be formed on a side of the electrode films which are the wire electrodes 3a and 3a, by the manufacturing method of the third embodiment as shown in FIG. 22. If pressure is applied to the state shown in the FIG. 22, the small width section 12 and the large width section 13 are not formed since the gap is not formed between the ceramic green sheets 2a and 2b, as exemplified in the third embodiment. Specifically, in this case, a configuration in which constant narrow electrode interval Dn is provided between the wire electrodes 3a and 4a, as shown in the first embodiment, can be provided.

According to the manufacturing method described, since the green ceramic green sheet 2d is disposed between the ceramic green sheets 2a and 2b, pressing is desirably applied without forming a level difference. As a result, insulation layers which surround the detection electrodes 3 and 4 of the detecting portion 11 are formed, and adherence is enhanced. The ceramic green sheets 2a, 2b and 2d are adhered together and ripping between the detection electrodes 3 and 4 is prevented. As a result, insulation properties and durability are enhanced.

Also, when the ceramic green sheet 2a corresponding to the narrow electrode interval Dn has a comparatively large thickness, an effect of the film thickness of the wire electrodes 3a and 4a is decreased. Specifically, when the ceramic green sheets 2a and 2b are laminated, the level difference due to the film thickness of sufficiently thin electrode wires 3a and 4a is almost not formed. In this case, the configuration of the first embodiment may be achieved without providing the ceramic green sheet 2d.

(Second Experiment 2)

Figure 23:
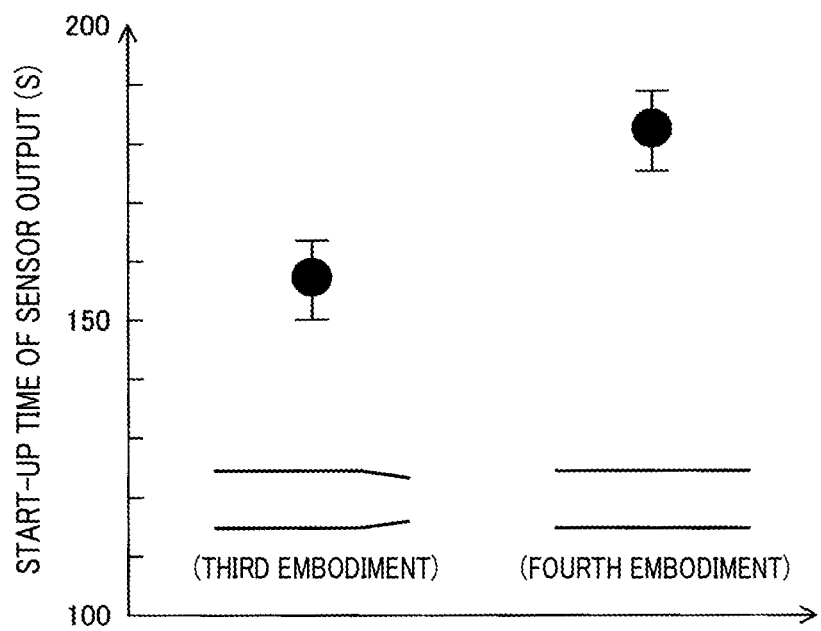
FIG. 23 is a diagram showing a relation between the disposed position of the detection electrodes of the detecting portion of the sensor element and the start-up time of the sensor output.

The start-up time of the sensor output, described in the first experiment 1, was investigated in the same way for the configurations of the third and fourth embodiment. For example, the start-up time of the sensor output of 180 seconds when the small width section 12 is not configured was shortened to 160 seconds when the small width section 12 is configured, as comparatively shown in FIG. 23. In this way, it was confirmed that by providing the detecting portion 11 with the small width section 12, a sensitivity of the entire sensor element 1 may be enhanced.

In the third embodiment, the laminate-type sensor element 1 is adapted, however, a configuration in which the plurality of wire detection electrodes 3a and 4a provided with small width sections 12 and large width sections 13 for the printed sensor element 1 of the second embodiment may also be adapted. Additionally, a configuration in which only a small width section 12 is provided on one end, without a large width section 13, may also be provided. As shown in the first embodiment, when either one or both of the electrode intervals Dw1 and Dw2 are configured in addition to the wide electrode interval Dw or in substitute of the wide electrode Dw, the large width section 13 may also be provided on each of the ends or on one of the ends thereof. In this case, the same electrode intervals or different electrode intervals may be configured on each of the large width sections 13.

As described above, the particulate matter detection sensor S is configured with the detecting portion 11 of the sensor element S. The detecting portion 11 is provided with the pair of the detection electrodes 3 and 4 which have the plurality of the electrode intervals Dn and Dw. As a result, the sensitivity of the sensor is maintained and variation in sensitivity may be decreased, without largely changing a structure of the detecting portion and manufacturing method. The frequency of an acute output due to the coarse particulate matter particles is decreased thus a detection precision may be enhanced.

As described in the fourth embodiment, the particulate matter detection sensor S is described as sensor which detects the particulate matter contained in the combustion gas of the internal combustion engine. However, the sensor S may be adapted for other engines, as long as the measuring gas contains particulate matter. The particulate matter detection sensor S is not presupposed to be used for DPF malfunction diagnosis. That is, the particulate matter detection sensor may be adapted for various usages. An internal combustion engine is not limited to a diesel engine and may also be used in gasoline engine for example.

The particulate matter detection sensor S is not limited to the above described embodiments, and may be modified without departing from the scope of the disclosure. For example, the cover body 5 which protects the sensor element 1 is preferably configured so that the measuring gas is introduced into the detecting portion 11 of the sensor element 1. The shape of the outer cover 51 and the inner cover 52, a size and number of the gas inlet/outlet holes, and an arranged position, for example, may be appropriately set. Additionally, the sensor element 1 is configured so that the detecting portion 11 has the detection electrodes 3 and 4 arranged on the surface of the insulating body 2, and a shape and material, for example of the insulating body 2 may be appropriately modified.

SYMBOLS

S particulate matter detection sensor
1 sensor element
11 detecting portion
2 insulating body
21 first insulation layer
22 second insulation layer
3 and 4 detection electrodes 3a and 4a wire electrodes
5 cover body

What is claimed is:

1. A particulate matter detection sensor comprising;
a sensor element configured to detect particulate matter contained in a measuring gas, the sensor element being provided with a pair of detection electrodes which consist of a positive electrode and negative electrode, the insulating body having a detecting portion provided on a surface of the insulating body, the pair of detection electrodes each having one side and being embedded to make the one side exposed on the detecting portion, the detecting portion having a surface with a center part; and
a cover body configured to cover an opening of a cylindrical housing which accommodates the sensor element, the cover body provided with gas inlet/outlet holes, the measuring gas being introduced and discharged through the gas inlet/outlet holes,
wherein each of the detection electrodes composing the one pair of detection electrodes is provided with a plurality of wire electrodes exposed on a front surface of the detecting portion, the wire electrode being electrically connected to the positive electrode and the wire electrode being electrically connected to the negative electrode alternately disposed in parallel to each other;
either one of a first insulation layer and a second insulation layer is disposed between two adjacent wire electrodes, among the wire electrodes, the first insulation layer configuring an electrode interval Dn as a first interval between two mutually adjacent wire electrodes of the detection electrodes, the second insulation layer configuring an electrode interval Dw as a second interval, the electrode interval Dw being configured as a wider interval than the interval Dn being a narrow interval, the second insulation layer having a plurality of insulation layers, the plurality of insulation layers having thicknesses which are different from each other, and
the first insulation layer is provided in the center part of the detecting portion.

2. The particulate matter detection sensor according to claim 1,
wherein the second insulation layer has an insulation layer positioned on a peripheral side of the detecting portion and an insulation layer positioned in a center part-side of the detecting portion, the insulation layer positioned on the peripheral side forming an electrode interval Dw1 and the insulation layer positioned in the center part side forming an electrode interval Dw2, and the electrode intervals are configured to satisfy a relation of Dn<Dw1<Dw2 with the electrode interval Dn.

3. The particulate matter detection sensor according to either claim 1,
wherein the second insulation layer is provided with an insulation layer positioned in a center part-side of the detecting portion and an insulation layer positioned on a peripheral-side of the detecting portion, the insulation layer positioned in the center part-side forming the electrode interval Dw1, and the insulation layer positioned on the peripheral-side forming the electrode interval Dw2, and the electrode intervals are configured to satisfy a relation of Dn<Dw1<Dw2 in relation to the electrode interval Dn.

4. The particulate matter detection sensor according to claim 1, wherein the first insulation layer and the second insulation being symmetrically disposed to each other are provided on both sides of the center part of the detecting portion, such that the center part of the detecting portion is intervened therebetween.

5. The particulate matter detection sensor according to claim 1, wherein
the detecting portion is configured with the second insulation layer and the first insulation layer being alternately disposed in an order of the second insulation layer and the first insulation layer, on an outer-side of the center part of the detecting portion.

6. The particulate matter detection sensor according to claim 1, wherein
the first electrode interval Dn is configured from 1 µm to 60 µm and the second electrode interval Dw is configured from 20 µm to 300 µm.

7. The particulate matter detection sensor according to claim 1, wherein
the sensor element is configured with an end surface of a length direction of the insulating body as a detecting portion, the insulating body being co-axially accommodated which in the cylindrical housing;
the cover body is provided with an outer cover and an inner cover being coaxially disposed thereon, and
the inner cover is provided with a plurality of the gas inlet/outlet holes which are arranged to surround the detecting portion with an equal distance therebetween each other.

8. The particulate matter detection sensor according to claim 1, wherein
the insulating body consists of a laminated body of insulation layers which include the first insulation layer and the second insulation layer;
electrode films which form the wire electrodes are exposed on the surface of the detecting portion, and
an entirety of the pair of the detection electrodes are surrounded by the insulation layers on the surface of the detecting portion.

9. The particulate matter detection sensor according to claim 8, wherein
the insulating body is provided with a third insulation layer disposed on a most outside layer in an element thickness direction, and
the first insulation layer is provided on an inner-side of the third insulation layer, on the surface of the detecting portion.

10. The particulate matter detection sensor according to claim 9, wherein
the third insulation layer has a layer thickness which is less or equal to three times the thickness of a the second insulation layer, the second insulation layer having a greater thickness than the first insulation layer.

11. The particulate matter detection sensor of claim 1, wherein the center
part of the detecting portion is a part on the surface thereof, the part including a predetermined gas flowed position.

12. A particulate matter detection sensor comprising;
a sensor element configured to detect particulate matter contained in a measuring gas, the sensor element being provided with a pair of detection electrodes which consist of a positive electrode and negative electrode, the insulating body having a detecting portion provided on a surface of the insulating body, the pair of detection electrodes each having one side and being embedded to make the one side exposed on the detecting portion, the detecting portion having a surface with a center part; and a cover body configured to cover an opening of a cylindrical housing which accommodates the sensor element, the cover body provided with gas inlet/outlet holes, the measuring gas being introduced and discharged through the gas inlet/outlet holes, wherein each of the detection electrodes composing the one pair of detection electrodes is provided with a plurality of wire electrodes exposed on a front surface of the detecting portion, the wire electrode being electrically connected to the positive electrode and the wire electrode being electrically connected to the negative electrode alternately disposed in parallel to each other;

either one of a first insulation layer and a second insulation layer is disposed between two adjacent wire electrodes, among the wire electrodes, the first insulation layer configuring an electrode interval Dn as a first interval between two mutually adjacent wire electrodes of the detection electrodes, the second insulation layer configuring an electrode interval Dw as a second interval, the electrode interval Dw being configured as a wider interval than the interval Dn being a narrow interval, and the second insulation layer having a plurality of insulation layers, the plurality of insulation layers having thicknesses which are different from each other; and wherein the first insulation layer and the second insulation being symmetrically disposed to each other are provided on both sides of the center part of the detecting portion, such that the center part of the detecting portion is intervened therebetween.

13. The particulate matter detection sensor according to claim 12, wherein
the second insulation layer has an insulation layer positioned on a peripheral side of the detecting portion and an insulation layer positioned in a center part-side of the detecting portion, the insulation layer positioned on the peripheral side forming an electrode interval Dw1 and the insulation layer positioned in the center part side forming an electrode interval Dw2, and the electrode intervals are configured to satisfy a relation of Dn<Dw1<Dw2 with the electrode interval Dn.

14. The particulate matter detection sensor according to claim 12, wherein
the second insulation layer is provided with an insulation layer positioned in a center part-side of the detecting portion and an insulation layer positioned on a peripheral-side of the detecting portion, the insulation layer positioned in the center part-side forming the electrode interval Dw1, and the insulation layer positioned on the peripheral-side forming the electrode interval Dw2, and the electrode intervals are configured to satisfy a relation of Dn<Dw1<Dw2 in relation to the electrode interval Dn.

15. The particulate matter detection sensor according to claim 12, wherein
the detecting portion is configured with the second insulation layer and the first insulation layer being alternately disposed in an order of the second insulation layer and the first insulation layer, on an outer-side of the center part of the detecting portion.

16. The particulate matter detection sensor according to claim 12, wherein the first electrode interval Dn is configured from 1 μm to 60 μm and the second electrode interval Dw is configured from 20 μm to 300 μm.

17. The particulate matter detection sensor according to claim 12, wherein the sensor element is configured with an end surface of a length direction of the insulating body as a detecting portion, the insulating body being co-axially accommodated which in the cylindrical housing;
the cover body is provided with an outer cover and an inner cover being coaxially disposed thereon, and
the inner cover is provided with a plurality of the gas inlet/outlet holes which are arranged to surround the detecting portion with an equal distance therebetween each other.

18. The particulate matter detection sensor according to claim 12, wherein the insulating body consists of a laminated body of insulation layers which include the first insulation layer and the second insulation layer;
electrode films which form the wire electrodes are exposed on the surface of the detecting portion, and
an entirety of the pair of the detection electrodes are surrounded by the insulation layers on the surface of the detecting portion.

19. A particulate matter detection sensor comprising;
a sensor element configured to detect particulate matter contained in a measuring gas, the sensor element being provided with a pair of detection electrodes which consist of a positive electrode and negative electrode, the insulating body having a detecting portion provided on a surface of the insulating body, the pair of detection electrodes each having one side and being embedded to make the one side exposed on the detecting portion, the detecting portion having a surface with a center part; and a cover body configured to cover an opening of a cylindrical housing which accommodates the sensor element, the cover body provided with gas inlet/outlet holes, the measuring gas being introduced and discharged through the gas inlet/outlet holes, wherein each of the detection electrodes composing the one pair of detection electrodes is provided with a plurality of wire electrodes exposed on a front surface of the detecting portion, the wire electrode being electrically connected to the positive electrode and the wire electrode being electrically connected to the negative electrode alternately disposed in parallel to each other;

either one of a first insulation layer and a second insulation layer is disposed between two adjacent wire electrodes, among the wire electrodes, the first insulation layer configuring an electrode interval Dn as a first interval between two mutually adjacent wire electrodes of the detection electrodes, the second insulation layer configuring an electrode interval Dw as a second interval, the electrode interval Dw being configured as a wider interval than the interval Dn being a narrow interval, and a plurality of the first insulation layers are provided in the center part of the detecting portion with the second insulation layer being positioned on an outer-side of the plurality of first insulation layers.

20. A particulate matter detection sensor comprising;
a sensor element configured to detect particulate matter contained in a measuring gas, the sensor element being provided with a pair of detection electrodes which consist of a positive electrode and negative electrode, the insulating body having a detecting portion provided on a surface of the insulating body, the pair of detection electrodes each having one side and being embedded to make the one side exposed on the detecting portion, the detecting portion having a surface with a center part; and a cover body configured to cover an opening of a cylindrical housing which accommodates the sensor element, the cover body provided with gas inlet/outlet holes, the measuring gas being introduced and discharged through the gas inlet/outlet holes, wherein each of the detection electrodes composing the one pair of detection electrodes is provided with a plurality of wire electrodes exposed on a front surface of the detecting portion, the wire electrode being electrically connected to the positive electrode and the wire electrode being electrically connected to the negative electrode alternately disposed in parallel to each other;

either one of a first insulation layer and a second insulation layer is disposed between two adjacent wire electrodes, among the wire electrodes, the first insulation layer configuring an electrode interval Dn as a first interval between two mutually adjacent wire electrodes of the detection electrodes, the second insulation layer configuring an electrode interval Dw as a second interval, the electrode interval Dw being configured as a wider interval than the interval Dn being a narrow interval;

the two mutually adjacent wire electrodes having the first insulation layer intervened therebetween are provided with small width sections;

the small width sections being disposed on an a tip end in an sensor element width direction are provided with electrode intervals Dn1, the small width sections being adjacent to each other at the electrode interval Dn1, the electrode interval Dn1 configuring an electrode interval which is narrower than the first electrode interval Dn, and the first insulation layer is provided in the center part of the detecting portion.

* * * * *

UNITED STATES PATENT AND TRADEMARK OFFICE
CERTIFICATE OF CORRECTION

PATENT NO. : 10,557,815 B2
APPLICATION NO. : 15/759947
DATED : February 11, 2020
INVENTOR(S) : Yamamoto et al.

Page 1 of 1

It is certified that error appears in the above-identified patent and that said Letters Patent is hereby corrected as shown below:

On the Title Page

Item (30), the Foreign Application Priority Data currently reads:
Sep. 15, 2015 (JP) .............................. 2015-182218

Should read:
Sep. 15, 2015 (JP) .............................. 2015-182218
Jul. 20, 2016 (JP) .............................. 2016-142329

Signed and Sealed this
Second Day of June, 2020

Andrei Iancu
*Director of the United States Patent and Trademark Office*